(12) United States Patent
Tandon et al.

(10) Patent No.: US 11,859,162 B2
(45) Date of Patent: Jan. 2, 2024

(54) METHOD AND APPARATUS FOR HIGH THROUGHPUT HIGH EFFICIENCY TRANSFECTION OF CELLS

(71) Applicant: The Charles Stark Draper Laboratory, Inc., Cambridge, MA (US)

(72) Inventors: Vishal Tandon, Somerville, MA (US); Charles A. Lissandrello, Newtonville, MA (US); Jenna L. Balestrini, Boston, MA (US); Jonathan R. Coppeta, Windham, NH (US); Patricia A. Swierk, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 1078 days.

(21) Appl. No.: 16/557,820

(22) Filed: Aug. 30, 2019

(65) Prior Publication Data

US 2020/0071727 A1 Mar. 5, 2020

Related U.S. Application Data

(60) Provisional application No. 62/725,382, filed on Aug. 31, 2018.

(51) Int. Cl.
*C12M 1/42* (2006.01)
*C12N 15/00* (2006.01)
(Continued)

(52) U.S. Cl.
CPC .......... *C12M 23/16* (2013.01); *C12M 35/02* (2013.01); *B01L 3/50273* (2013.01);
(Continued)

(58) Field of Classification Search
CPC ...... C12M 35/02; C12M 23/16; C12M 41/48; C12M 23/44; C12N 15/87
See application file for complete search history.

(56) References Cited

U.S. PATENT DOCUMENTS 6,090,617 A * 7/2000 Meserol ................ C12N 13/00
435/173.6
6,773,669 B1 8/2004 Holaday et al.
(Continued)

FOREIGN PATENT DOCUMENTS

CN 107 988 070 5/2018
JP 2007007430 A 1/2007
(Continued)

OTHER PUBLICATIONS

Cho et al., A high throughput microelectroporation device to introduce a chimeric antigen receptor to redirect the specificity of human T cells (Biomed Microdevices, 2010, 12:855-863) (Year: 2010).*
(Continued)

*Primary Examiner* — Arthur S Leonard
(74) *Attorney, Agent, or Firm* — HoustonHogle LLP

(57) ABSTRACT

Transfer of genetic and other materials to cells is conducted in a hands-free, automated, high throughput, continuous process. A system using a microfluidic hydrodynamic sheath flow configuration includes arrangements for pushing cells from side streams containing a cell culture medium to a central stream containing an electroporation buffer. Electroporation can be conducted in an assembly in which two or more microfluidic channels are provided in a parallel configuration and in which various layers can be stacked together to form a laminate type structure.

18 Claims, 16 Drawing Sheets

(51) Int. Cl.
*C12M 3/06* (2006.01)
*B01L 3/00* (2006.01)
*C12N 15/87* (2006.01)

(52) U.S. Cl.
CPC ... *B01L 3/502715* (2013.01); *B01L 2300/047* (2013.01); *B01L 2300/087* (2013.01); *B01L 2300/0864* (2013.01); *B01L 2300/0887* (2013.01); *B01L 2400/0496* (2013.01); *C12N 15/87* (2013.01)

(56) References Cited

U.S. PATENT DOCUMENTS

| 7,029,916 | B2 | 4/2006 | Dzekunov et al. | |
| 7,141,425 | B2 * | 11/2006 | Dzekunov | A61N 1/0412 |
| | | | | 435/461 |
| 11,225,638 | B2 * | 1/2022 | Corso | C12M 35/02 |
| 2009/0053686 | A1 | 2/2009 | Ward et al. | |
| 2014/0256047 | A1 | 9/2014 | Lee et al. | |
| 2017/0283761 | A1 | 10/2017 | Corso | |

FOREIGN PATENT DOCUMENTS

| JP | 2017537615 A | 12/2017 | | |
| JP | 2021530983 A | 11/2021 | | |
| WO | WO-02072235 A1 * | 9/2002 | | A61M 1/3472 |
| WO | WO 2016077761 | 5/2016 | | |
| WO | WO 2017040995 | 3/2017 | | |

OTHER PUBLICATIONS

International Preliminary Report on Patentability, dated Mar. 11, 2021, from International Application No. PCT/US2019/049210, filed on Aug. 30, 2019. 14 pages.
International Search Report and Written Opinion, completed on Mar. 17, 2020, from International Application No. PCT/US2019/049210, filed on Aug. 30, 2019. 19 pages.
Aijaz, A., et al., "Biomanufacturing for clinically advanced cell therapies," Nat. Biomed. Eng., 2)6): 362-376 (2018).
Anonymous, "A Chance for Complete Remission," First Car T Therapy for Non-Hodgkin Lymphoma | YESCARTA R (axicabtagene ciloleucel) https://www.yescarta.com/ (2019).
Anonymous, "A New Idea in Magnetic Stirrers," https://www.vp-scientific.com/Alnico_&_Rare_Earth_Stir_Bars.php#VP772FS-25-55TF (2010).
Anonymous, "KYMRIAH (tisagenlecleucel)| Childhood Acute Lymphoblastic Leukemia Treatment," https://www.us.kymriah.com/acute-lymphoblastic-leukemia-children/ 1-5 (2019).
Anonymous, "MaxCyte GT," https://www.maxcyte.com/products-services/gt/, 1-5 (2019).
Augustsson, P., et al., "Buffer medium exchange in continuous cell and particle streams using ultrasonic standing wave focusing," Microchim Acta, 164: 269-277 (2009).
Bernhardt, J., et al., "On the generation of potential differences across the membranes of ellipsoidal cells in an alternating electrical field," Biophysik, 10 (3): 89-98 (1973).
Brudno, J. N., et al., "Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease," J. Clin. Oncol., 34(10): 1112-1121 (2016).
Cervia, L. D., et al., "Distinct effects of endosomal escape and inhibition of endosomal trafficking on gene delivery via electrotransfection," PLoS ONE, 12(2): 1-18 (2017).
Chang, C. C., et al., "Role of specific endocytic pathways in electrotransfection of cells," Mol. Ther.—Methods Clin. Dev., 1: 14058 (2014).
Escoffre, J. M., et al., "What is (Still not) known of the mechanism by which electroporation mediates gene transfer and expression in cells and tissues," Mol. Biotechnol., 41(3): 286-295 (2009).

Geng, T., et al., "Microfluidic electroporation for cellular analysis and delivery," Lab on a chip, 13(19): 3803-3821 (2013).
Gowrishankar, T. R., et al., "Microdosimetry for conventional and supra-electroporation in cells with organelles," Biochem. Biophys. Res. Commun., 341(4): 1266-1276 (2006).
Hibino, M., et al., "Time courses of cell electroporation as revealed by submicrosecond imaging of transmembrane potential," Biophys. J., 64(6): 1789-1800 (1993).
Hsi, P., et al., "Acoustophoretic Rapid Media Exchange and Continuous-Flow Electrotransfection of Primary Human T Cells for Applications in Automated Cellular Theraphy Manufacturing," Lab on a Chip, 1-15 (2019).
June, C. H., et al., "CAR T cell immunotherapy for human cancer," Science, 359 (6382): 1361-1365 (2018).
Kochenderfer, J. N., et al., "Treating B-cell cancer with T cells expressing anti-CD19 chimeric antigen receptors," Nat. Rev. Clin. Oncol., 10(5): 267-276 (2013).
Kotnik, T., et al., "Analytical Description of Transmembrane Voltage Induced by Electric Fields on Spheroidal Cells," Biophysical Journal, 79(2): 670-679 (2000).
Krassowska, W., et al., "Modeling electroporation in a single cell," Biophys. J., 92: 404-417 (2007).
Lee, C. S., et al., "Adenovirus-mediated gene delivery: Potential applications for gene and cell-based therapies in the new era of personalized medicine," Genes Dis., 4(2): 43-63 (2017).
Lee, G.-B., et al., "The Hydrodynamic Focusing Effect Inside Rectangular Microchannels," J. Micromech. Microeng., 16: 1024-1032 (2006).
Levine, B. L., et al. "Global Manufacturing of CAR T Cell Therapy," Mol. Ther.—Methods Clin. Dev., 4: 92-101 (2017).
Liu, F., et al., "Mechanism of in vivo DNA transport into cells by electroporation: Electrophoresis across the plasma membrane may not be involved," J. Gene Medicine, 8: 353-361 (2006).
Mao, M., et al., "Involvement of a Rac 1-Dependent Macropinocytosis Pathway in Plasmid DNA Delivery by Electrotransfection," Mol. Ther., 25(3): 803-815 (2017).
Marcucci, K. T., et al., "Retroviral and Lentiviral Safety Analysis of Gene-Modified T Cell Products and Infused HIV and Oncology Patients," Mol. Ther., 26(1): 269-279 (2018).
Mescher, M. J., et al., "Fabrication methods and performance of low-permeability microfluidic components for a miniaturized wearable drug delivery system," J. Microelectromechanical Syst., 18(3): 501-510 (2009).
Milone, M.C., et al., "Clinical use of lentiviral vectors," Leukemia, 32(7): 1529-1541 (2018).
Moiseyenko, R.P., et al., "Whole-System Ultrasound Resonances as the Basis for Acoustophoresis in All-Polymer Microfluidic Devices," Phys. Rev. Appl., 11, 014014-1-014014-14 (2019).
Petersson, F., et al., "Carrier Medium Exchange through Ultrasonic Particle Switching in Microfluidic Channels," Anal. Chem., 77(5): 1216-1221 (2005).
Poirot, L., et al., "Multiplex genome-edited T-cell manufacturing platform for "off-the-shelf" adoptive T-cell immunotherapies," Cancer Res., 75(18): 3853-3864 (2015).
Pucihar, G., et al., "The Influence of Medium Conductivity on Electropermeabilization and Survival of Cells in Vitro," Bioelectrochemistry, 54: 107-115 (2001).
Rashid, M., et al., "Serum-Reduced Media Impacts on Cell Viablility and Protein Expression in Human Lung Epithelial Cells," J. Cell Physiol, 234: 7718-7724 (2019).
Rols, M. P., et al., "Electropermeabilization of mammalian cells to macromolecules: Control by pulse duration," Biophys. J., 75(3): 1415-1423 (1998).
Rols, M. P., et al., "Electropermeabilization of mammalian cells. Quantitative analysis of the phenomenon," Biophys. J., 58(5): 1089-1098 (1990).
Rols, M.-P., et al., "Flow Cytometry Quantification of Electropermeabilization," Methods in Molecular Biology, 91: 141-147 (2019).
Rosazza, C., et al., "Gene Electrotransfer: A Mechanistic Perspective," Curr. Gene Therapy, 16(2): 98-129 (2016).

(56) References Cited

OTHER PUBLICATIONS

Schwan, H. P., "Biophysics of the Interaction of Electromagnetic Energy with Cells and Membranes," In Biological Effects and Dosimetry of Nonionizing Radiation, 213-231, (Springer US, Boston, MA, 1983).

Stewart, M. P., et al., "Intracellular delivery by membrane disruption: Mechanisms, strategies, and concepts," Chem. Rev., 118(16): 7409-7531 (2018).

Sukhorukov, V.L., et al., "Surviving high-intensity field pulses Strategies for improving robustness and performance of electrotransfect," J. Membrane Biol., 206: 187-201 (2005).

Tandon, V., et al., "Microfabricated infuse-withdraw micropump component for an integrated inner-ear drug-delivery platform," Biomed. Microdevices, 17(37): 1-16 (2015).

Tandon, V., et al., "Microfabricated reciprocating micropump for intracochlear drug delivery with integrated drug/fluid storage and electronically controlled dosing," Lab Chip, 16(5): 829-846 (2016).

Teissié, J., et al., "An experimental evaluation of the critical potential difference inducing cell membrane electropermeabilization," Biophys. J., 65(1): 409-413 (1993).

Tieleman, D. P., "The molecular basis of electroporation," BMC Biochem., 5: 1-12 (2004).

Van Meirvenne, S., et al., "Efficient genetic modification of murine dendritic cells by electroporation with mRNA," Cancer Gene Ther., 9(9): 787-797 (2002).

Weaver, J. C., et al., "Theory of electroporation: A review," Bioelectrochemistry Bioenerg., 41: 135-160 (1996).

Wei, Z., et al., "A Laminar Flow Electroporation System for Efficient DNA and SiRNA Delivery," Anal. Chem., 83(15): 5881-5887 (2011).

Wu, M., et al., "Membrane binding of plasmid DNA and endocytic pathways are involved in electrotransfection of mammalian cells," PLoS ONE, 6(6): E20923 (2011).

Zhao, Y., et al., "High-efficiency transfection of primary human and mouse T lymphocytes using RNA electroporation," Mol. Therapy: Journal Am. Soc. Gene Ther., 13(1): 151-159 (2006).

Zheng, M., et al., "Hydrodynamically controlled cell rotation in an electroporation microchip to circumferentially deliver molecules into single cells," Microfluid. Nanofluidics, 20(16): 1-12 (2016).

Zhu, T., et al., "Electroporation Based on Hydrodynamic Focusing of Microfluidics with Low DC Voltage," Biomed Microdevices, 12: 35-40 (2010).

Partial Search Report, dated Dec. 11, 2019, from International Application No. PCT/US2019/049210, filed on Aug. 30, 2019. 13 pages.

Lee, G-B. et al., "Continuous medium exchange and optically induced electroporation of cells in an integrated microfluidic system", Microsystems & Nanoengineering, Jun. 15, 2015, vol. 1, No. 1, DOI: 10.1038/micronano.2015.7, pp. 1-10.

* cited by examiner

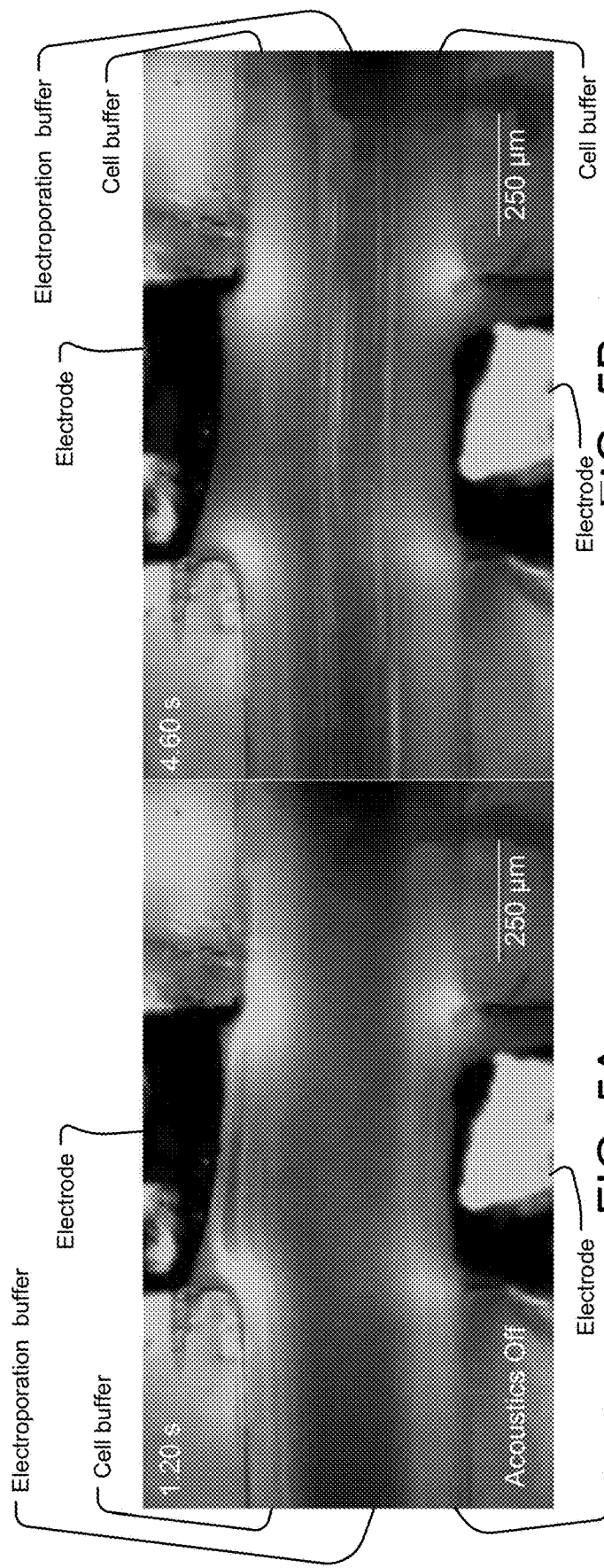

METHOD AND APPARATUS FOR HIGH THROUGHPUT HIGH EFFICIENCY TRANSFECTION OF CELLS

RELATED APPLICATIONS

This application claims the benefit under 35 USC 119(e) of U.S. Provisional Application No. 62/725,382, filed on Aug. 31, 2018, which is incorporated herein by reference in its entirety.

BACKGROUND OF THE INVENTION

Many applications in biology, medicine, pharmaceutical research and other areas use techniques in which genetic materials are introduced into cells. The term "transformation" is often used when working with bacteria or non-animal eukaryotic cells, including plant cells. "Transfection" almost always refers to work on eukaryotic cells, while "transduction" typically applies to virus-mediated gene transfer into eukaryotic cells.

Materials of interest can include not only DNA, siRNA, mRNA, RNP complexes, but also small molecules or proteins such as antibodies. In many cases, the transfer of such a "cargo" material involves opening transient pores or "holes" in the cell membrane to allow its uptake and thus alter or genetically modify the cells.

One common technique used to temporarily permeabilize cells is electroporation. Parameters considered when developing electroporation procedures include cell properties (cell size, shape, membrane structure, surface charge, for example), the cell environment, and attributes of the applied electric field, (e.g., pulse intensity, number of pulses, pulse duration, pulse shape and/or frequency). It is generally believed that membrane permeabilization during electroporation occurs after the applied electric field induces a threshold value in the transmembrane potential or "electroporation threshold" and that, at a given applied electric field, there is a threshold for the number of pulses and pulse length, needed for successful electroporation. The Schwan equation and related derivations are often used to estimate a cell's transmembrane potential that develops in response to relevant experimental parameters including applied field, cell size, conductivities of media, cellular cytosol, and cell membrane, and membrane thickness ("Analytical Description of Transmembrane Voltage Induced by Electric Fields on Spheroidal Cells", Biophysical Journal, Volume 79 August 2000 670-679).

SUMMARY OF THE INVENTION

Traditionally, the genetic modification of cells by electroporation has been conducted as a bulk, batch process using cuvettes. Less prevalent, commercial devices that might employ a flow configuration lack some automated features.

For instance, existing electroporation processes often employ specialized, low-conductivity buffers that can negatively impact cell viability, especially with prolonged exposure. Batch processing, therefore, requires several buffer exchanges and wash steps, that render the approach touch-labor intensive and difficult to scale up to meet growing large-batch manufacturing needs. Manual wash and/or filtration steps are also slow, so cells are still exposed to electroporation buffer for time scales on the order of minutes up to about an hour. These steps often are associated with cell loss (low cell recovery). Absent too is a high throughput transfection system.

As cellular therapies move toward large-scale production using allogenic rather than autologous sources of cells, bioprocessing of cellular therapies using bulk methods are increasingly becoming intractable.

In addition, commercially available electroporation devices expose biologics to direct contact with electrodes, resulting in potential damage due to local heating and Faradaic by-products (hydronium ions, hydroxyl ions, chlorine, free radicals, and electrode breakdown by-products (e.g. aluminum ions and particulate)). Without microfluidics, many traditional electroporation approaches cannot transport heat away from thermally susceptible biological entities or cannot do this efficiently. In some cases, there is a lack of co-localization of cells (or other substrates) and payload (cargo), leading to inefficiencies and losses of (valuable) materials.

A need exists, therefore, for equipment and procedures that address at least some of the problems discussed above.

Described herein are approaches in which transfer of genetic or other materials to cells is conducted in a hands-free, automated, high throughput, continuous process.

Some embodiments rely on a microfluidic hydrodynamic sheath flow configuration and include arrangements for pushing cells from side streams containing, for example, a cell culture medium, to a central stream containing an electroporation buffer. Electroporation can be conducted in an assembly in which two or more microfluidic channels are provided in a parallel configuration and in which various layers can be stacked together to form a laminate type structure. Each microfluidic channel is provided with a pair of electrodes, preferably constructed to withstand long-lasting, continuous and high throughput operations.

In one implementation the device is part of a system that includes common reservoirs, a pumping system for driving fluids to and/or from the reservoirs, a voltage generator for electroporation and a controller for the partial or complete automation of the system. At least one incubator can be used for the storage of cells. Specific arrangements include agitation to prevent cells from settling.

Other embodiments feature a method in which cells from an incubator are directed to a device in which cells are driven from cell culture conditions into an electroporation buffer and electroporated. Cells containing a cargo can then be transferred back into culture conditions and/or collected. In specific implementations, the payload-containing cells are administered to a subject in need of diagnosis, prophylaxis or treatment.

In some of its aspects, the invention can be used in cellular therapy manufacturing. As an example, techniques and equipment described herein can be used in the electrotransfection of primary T cells with mRNA. In other aspects, cargo-containing cells produced using approaches described herein are administered to a subject in need of treatment, prophylaxis or diagnosis.

Practicing the invention can address problems encountered with conventional systems and can have many advantages. For example, the equipment and techniques described herein can reduce or minimize the duration of exposure of cells to non-ideal conditions (electroporation buffer, room temperature) and loss of cells and/or genetic material associated with conventional buffer exchanges. It has been demonstrated, for example, that both transfection efficiency and cell health are detrimentally affected by long-term exposure (~30 min or longer) to storage in electroporation buffer at room temperature. Approaches disclosed herein can decrease these types of exposure to less than 1 minute or can precisely control the residence time of cells within a solution to the exact desired length in a continuous fashion (e.g., 20 minutes in solution A, 3 minutes in solution B, 1 min in solution C).

In many embodiments, cell handling is automated during the entire process for transferring cargo into cells or other membrane bound substrates, such as transfection procedures. Thus, in contrast to existing commercial devices, the system described herein can house cells under cell-culture conditions in an automated way as part of a process flow. Buffer exchanges are no longer performed manually, using centrifugation and resuspension of cells. Rather, in many of its aspects, the invention offers an automated way of achieving buffer exchanges. Also possible are configurations in which the cells and/or materials being transferred can be protected from direct contact with the electroporation electrodes.

Through techniques described herein, large numbers of cells can be processed continuously, with high throughput and for extended period of times. Assemblies that include multiple microfluidic channels, e.g., in the parallel configuration described herein, can utilize common components such as common reservoirs, pumping system, electric field generator and so forth, simplifying the overall layout.

Robust, flexible and versatile, embodiments of the invention can be applied or adapted to various types of cargo, cells or other membrane-bound substrates (structures such as other types of vesicles or exosomes). Although the electroporation and/or other modules disclosed herein can be disposable (after one use, for example), the designs presented yield devices that are sufficiently strong and sturdy for repeated use.

Principles described herein also can be employed to remove some or all of the contents held in cells or other membrane bound structures; that is, opening pores and allowing the internal contents to diffuse out either passively or via active mechanisms such as acoustophoretic or electrophoretic forces.

In general, according to one aspect, the invention features a method for introducing a payload into cells. The method comprises directing cells from a first incubator to an assembly that contains multiple microfluidic devices, driving cells from a cell culture medium to an electroporation medium, applying an electric field to cells in the electroporation medium in a sheath flow configuration in which the electroporation medium flows in a central stream, and transferring or allowing the transfer of the payload into the cells.

In embodiments, the method can further comprise driving cells containing the payload from the electroporation fluid into a cell culture fluid. In addition, the cells containing the payload are stored in a second incubator.

Often, the cells containing the payload are administered to a subject in need of diagnosis, prophylaxis or treatment.

In general, according to another aspect, the invention features a method for manufacturing cells for immunotherapy, the method comprising transferring cells from a first buffer, wherein the first buffer is a cell culture medium, into an electroporation buffer and then permeabilizing the cells by electroporation. This allows a payload to transfer into the permeabilized cells. Then, the cells containing the payload are transferred into a second buffer. The invention entails an automated and continuous flow mode and the throughput might be at least 4 million cells per minute.

In general, according to another aspect, the invention features a system for an automated, continuous flow transfer of cargo into cells. This system comprises a first incubator for storing cells, an electroporation assembly comprising a layer supporting multiple microfluidic channels disposed in a parallel configuration, a first buffer exchanger for driving cells from a cell culture medium to an electroporation medium, a second buffer exchanger for driving cells from the electroporation medium into a culture medium, and a controller.

Preferably, the system includes a pump system for delivering electroporation buffer to the electroporation assembly, for delivering cells to the first buffer exchanger and/or for delivering cells from the second buffer exchanger to a second incubator. Further, each microfluidic channel might have trifurcating inlets and outlets, which might be configured to support a central stream and side sheath streams.

In general, according to another aspect, the invention features an electroporation assembly, comprising: a channel layer including at least two microfluidic channels arranged in a parallel configuration, an electrode layer including a pair of electrodes for each microfluidic channel, a port layer for fluid connections to trifurcating inlets and outlets of the microfluidic channels, wherein the layers are stacked in a laminate configuration.

In general, according to another aspect, the invention features a system for bulk transfer of cargo into cells, comprising: an incubator for maintain the cells at a desired temperature, an agitator apparatus for preventing the cells from settling in the incubator, a buffer exchanger for moving the cells into an electroporation buffer, a flow electroporation device for electroporating the cells in electroporation buffer to transfer the cargo, and an incubator for receiving the cells from the flow electroporation device.

The agitator apparatus might comprise an impeller within a cell reservoir. In addition, a pump might be used between the incubator and the buffer exchanger. Also, a pump for flowing electroporation buffer into the buffer exchanger is helpful. Also, a fluidic capacitor is helpful between the incubator and the buffer exchanger.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 5A (acoustics off) and 5B (acoustics activated) are microscopy images demonstrating acoustically-driven rapid buffer exchange processes.

DETAILED DESCRIPTION OF THE PREFERRED EMBODIMENTS

Figure 1:
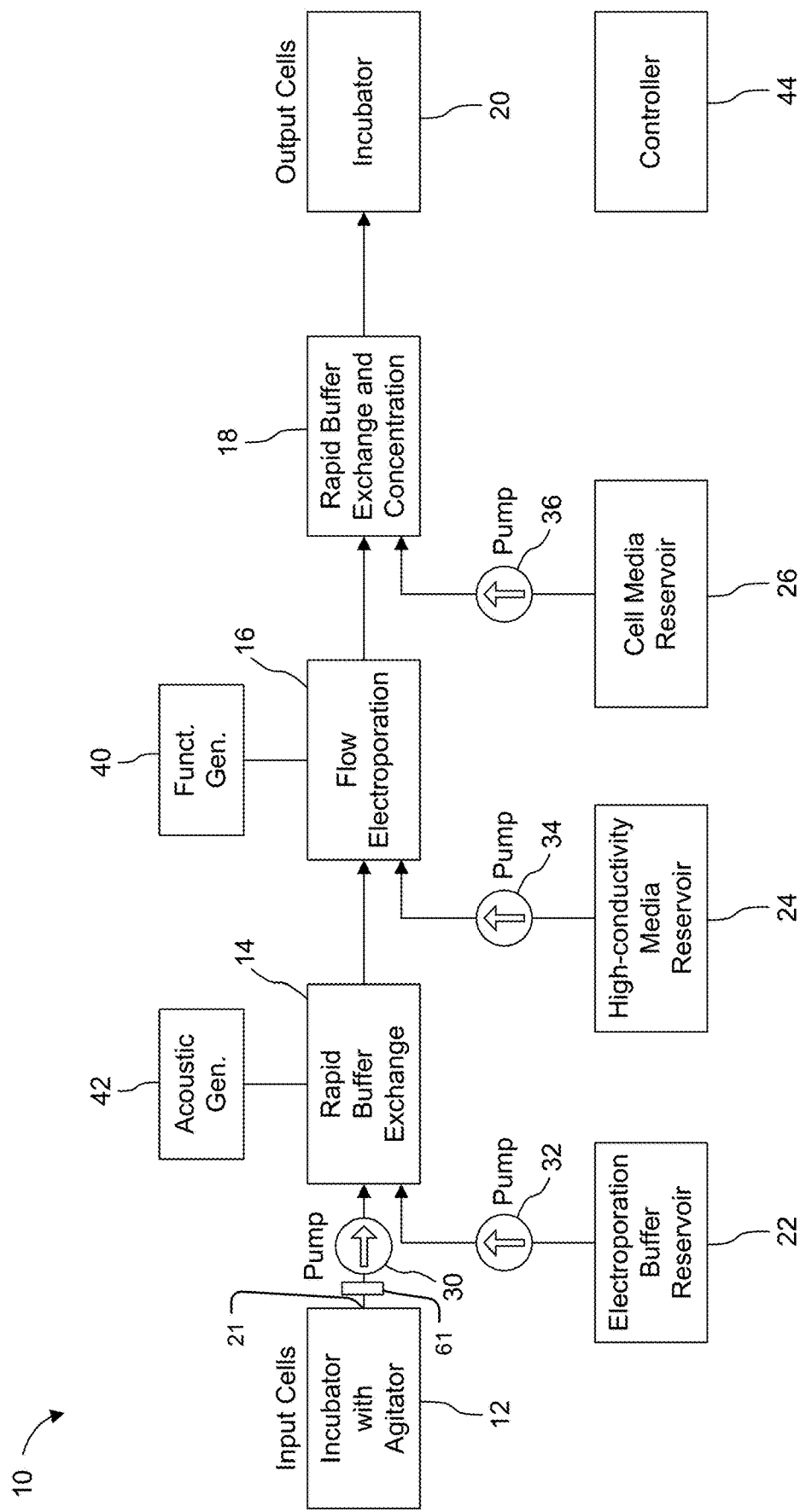
FIG. 1 is a schematic diagram showing an apparatus for a hands-free, continuous flow transfection of cells.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention generally relates to approaches for transferring one or more material(s) or agent(s), referred to herein as "cargo" or "payload", into or out of cells. In many cases, the cells are eukaryotic cells, typically having a diameter within the range of from about 10 to about 100 microns ($\mu$m). Cargo also can be transferred to or from other membrane bound structures, such as, for instance, liposomes, exosomes, micelles, etc.

Examples of cargo materials include but are not limited to small molecules, chromosomes, DNA, RNA, (e.g., mRNA, siRNA, gRNA, ssRNA), other genetic materials, oligomers, biomarkers, proteins, transposons, biomolecule complexes, small molecules, therapeutic agents, and so forth. Often, the cargo is an agent useful in the treatment, prophylaxis or diagnosis of a condition in a human or animal subject.

In many of its aspects, the invention relates to a system that supports a hands-free, continuous flow transfer of cargo to cells or other substrates. Processes conducted in the system can be partially or completely automated.

Shown in FIG. 1, for example, is system 10 which includes several components or modules: incubator 12, (first) buffer exchanger 14, electroporation assembly 16, (second) buffer exchanger 18 and (second) incubator 20. The system can further include one or more reservoirs such as reservoirs 22, 24 and 26, for example and pumps 30, 32, 34 and 36. Voltages required for electroporation are provided by electrical function generator 40 and acoustic energy is provided via acoustic function generator 42. The system is controlled by controller 44. Often the controller is a microprocessor in a computer system such as a single board computer system. In other cases, the controller is a microcontroller with integrated memory and analog to digital converters and digital to analog converters.

Either or both incubators 12 and 20 (disposed, respectively, upstream of and downstream of electroporation assembly 16) can be benchtop incubation chambers configured for housing cells before and/or after electroporation and can have an internal volume of about 0.3 to about 50 liters (L). In many cases one or both incubators have a miniaturized design.

Typically, incubator 12 and/or 20 is/are provided with means for transferring cells to and/or from the incubators.

For example, incubator 12 can be equipped with a receptacle for a cell container or reservoir (a flask, conical tube, etc.). The container can be a sealed, sterile container such as a blood bag, for instance. In illustrative examples, it provides cells at a concentration of $10^5$ to $5 \times 10^8$ cell/mL) suspended in a high-conductivity (e.g., about 1 to 2 S/m) culture buffer, such as TexMACS or RPMI (Roswell Park Memorial Institute) medium for T cells.

A closed loop or another suitable arrangement can be included to control the cell culture conditions, e.g., the incubator temperature (often maintained at 37° C.), the incubator gas composition ($CO_2$ and/or humidity levels, for instance), sensors for metabolic or general processing readouts (pH, $O_2$, etc.) and so forth.

Examples of cells that can be housed in incubator 12 include suspension cells such as primary T cells, NK cells, hematopoietic stem cells, or adherent cells such as MSCs, CHO cells, and many others. In some implementations, incubators 12 and/or 20 are designed or adapted to support membrane-bound structures such as liposomes, exosomes, micelles and so forth. Suitable buffers and conditions for keeping these targets stable can be selected as known in the art and/or determined experimentally.

With cells (or other membrane-bound structures) that may not be neutrally buoyant in the culture medium, the incubator can be fitted with an agitation mechanism for generating a (gentle) movement in the container that houses the cells, reducing, minimizing or preventing settling or sinking. This helps to ensure that the concentration of cells that is delivered into downstream operations (media exchange and electroporation) is controlled and consistent. One illustrative design is described below with reference to FIG. 2.

In some cases, rather than utilizing separate incubator chambers for the start and end of the process (see, e.g., elements 12 and 20 in FIG. 1), the entire system is housed in an incubator chamber.

In many of the embodiments described herein, electroporation assembly 16 supports electroporation processes conducted in continuous fashion, using a sheath flow configuration, in a microfluidic channel, for example. One specific implementation brings cells and cargo into contact in a central flow or stream, that typically utilizes a low conductivity fluid, also referred to herein as an electroporation fluid. The central stream flows between two sheath (also referred to as "side" or "lateral") streams that typically employ high conductivity fluids. The difference in conductivity between the center and side fluids leads to a concentration of the electric field (supplied by voltage generator 40) in the central (low-conductivity) region of the flow, allowing an effective amplification of the electric field strength and preventing cells in the central stream from coming into physical contact with the electrodes.

Considering that preferred media for cell cultures typically have high electrical conductivity and the sheath flow arrangement described above preferably places the cells in a low conductivity medium during electroporation, system 10 uses buffer exchange arrangement 14 for transferring cells from the cell culture medium to an electroporation buffer medium. In many embodiments, the rapid buffer exchange represented by component 14 in FIG. 1 involves driving cells from one flow stream into another acoustically, with acoustic frequencies being generated through component 42.

After electroporation, cells can be transferred from the electroporation medium into a cell medium. One approach illustrated in FIG. 1 employs buffer exchange module 18 which can further include a cell concentration function. Traditionally, cell concentration is typically accomplished in batch processes using centrifugation, but could be accomplished in flow configurations using acoustophoresis, dielectrophoresis, electrophoresis, inertial effects, or integrated porous membranes or sieves.

In one embodiment, at least one of buffer exchange devices 14 and 18 is a rapid buffer exchange device and cell concentrator. Another embodiment utilizes a design in which one or both buffer exchange (switching) modules and the electroporation device 16 (which can employ the sheath flow configuration described above) are integrated into a single apparatus. In a further embodiment, at least one buffer exchange is conducted in a device that is separate from the electroporation device. In one example of this approach, buffer exchanger 14, flow electroporation assembly 16 and buffer exchanger 18 are connected to one another by conduits, e.g., suitable tubing, that can provide fluid communication between these components.

Some aspects of the invention employ acoustically-driven rapid buffer switching in both devices 14 and 18. In other aspects, non-acoustically-driven buffer switching is utilized in at least one of the buffer exchange devices. One implementation utilizes an acoustically-driven buffer exchange device 14 and a non-acoustically-driven buffer exchange device 18.

Construction and operational details for acoustically-driven buffer exchanges are provided in U.S. patent application Ser. No. 16/359,626, with the title Acoustically-Driven Buffer Switching for Microparticles, filed on Mar. 20, 2019, which is incorporated herein by this reference. Techniques that can be employed to obtain non-acoustically driven buffer switching include but are not limited to inertial techniques, microchannels with integrated porous membranes or sieves, or diffusion-b based techniques.

Output cells are collected in incubator 20. In one example, these cells are primary human T cells that contain mRNA. Such cells can be used in gene editing applications, or as transient therapeutic systems (mRNA CAR-T). In other examples, the output cells are used for protein or extracellular vesicle production (e.g., modified CHO cells or MSCs).

Throughout the system, flow is driven (actuated) by a pump system, including pumps that are commercial, off-the shelf pumps often of peristaltic design. Other suitable pump types can be employed. In general, one pump is used to actuate flow of the cell suspension out of the first incubation chamber and through the entire system with a flow rate that ranges, e.g., from 100 µL/min to 2 mL/min. One additional pump is needed for each buffer exchange that occurs in the system. Nominally, at least two pumps are needed: one involved in moving cells into the electroporation buffer, and one that later returns cells to a culture buffer. In order to protect against flow rate differentials between devices, fluidic capacitors or reservoirs can be placed between devices that act as ballast. In this case, each microfluidic device has its own set of pumps to control flow rate.

In system 10, cells to be electroporated are withdrawn from incubator 12 using pump 26, which can be a syringe pump capable of controlling fluid flow. System 10 also includes reservoir 22 and pump 32, e.g., a syringe pump, for supplying electroporation buffer to electroporation arrangement 16. High conductivity fluid for the sheath flow can be added from reservoir 24 by means of pump 34, e.g., a syringe pump. Cell medium is supplied to buffer exchange module 18 from reservoir 26, using pump 36, e.g., a syringe pump.

System 10 provides various options regarding the reservoir that houses the cargo to be incorporated into the cells (or into other types of membrane bound structures. In one example that uses primary human T cells, mRNA in electroporation buffer can be introduced from reservoir 22 into media exchange device 14, which transfers cells into the mRNA-laden electroporation media before it flows into electroporation device 16. Other arrangements supply a cargo such as plasmid DNA, single-stranded linear DNA, double-stranded linear DNA, linearized plasmid DNA, single-stranded donor oligonucleotides, ribonucleoproteins (e.g., Cas9 protein complexed with guide RNA), proteins, or small molecules from reservoir 22. Cells can also be manually suspended in electroporation media laden with cargo, introduced into incubator 12, and the flowed directly into flow electroporation device 16.

Silastic or other suitable tubing can be employed for some or all connections providing fluid communication between the various modules (components).

Controller 44 can include one or more computers, hardware, software, sensors, interfaces, etc. for controlling the operation of system 10 or components thereof, to reach partial or complete automation. In many embodiments, controller 44 controls the electrical parameters applied for electroporation and/or the acoustic frequencies employed in buffer exchange device 14 and, optionally, in buffer exchange device 18. Controller 44 can monitor or control incubator parameters, the operation of one or more of pumps 30, 32, 34 and/or 36, the flow and parameters of central and/or sheath streams described above and so forth.

Various embodiments that can be included in system 10 and/or its operation are further described below.

For instance, as noted above, system 10 can utilize one or more agitators for preventing cells maintained in an incubator from settling. An example is presented in FIGS. 2A and 2B. Shown in these drawings is front end agitator apparatus 11, which can be housed in incubator 12 (FIG. 1). Agitator apparatus 11 includes a cell reservoir 13 for supplying cells in a suitable cell buffer to buffer exchanger 14 (FIG. 1) and impeller 15, for stirring the cells and keeping them from settling. In specific embodiments, cell reservoir 13 includes a cylindrical (tubular) upper section 17 and a conical lower section 19. Outlet 21 provides fluidic communication between the conical lower section 19 of cell reservoir 13 to pump 30 in FIG. 1. A lid 23 caps the top opening of section 17.

Cell reservoir 13 can have a volume within the range of from about 15 mL to about 1 L.

Figure 2B:
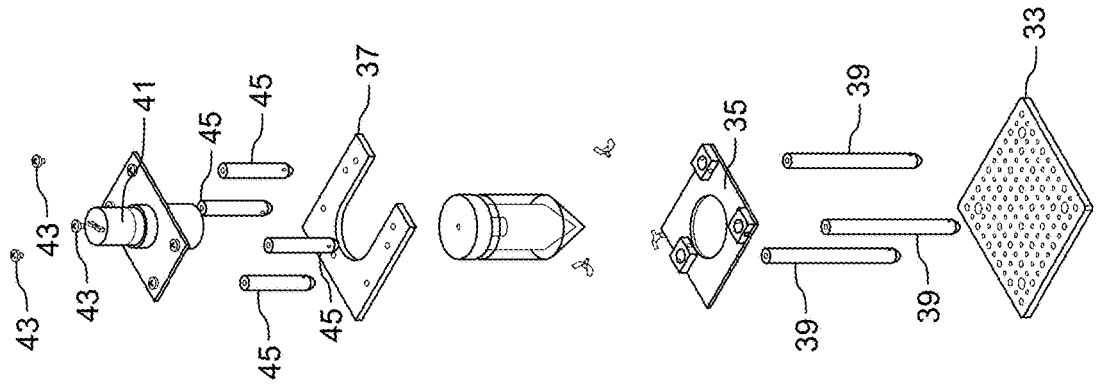
FIG. 2B is an exploded view of the apparatus in FIG. 2A.
Figure 2A:
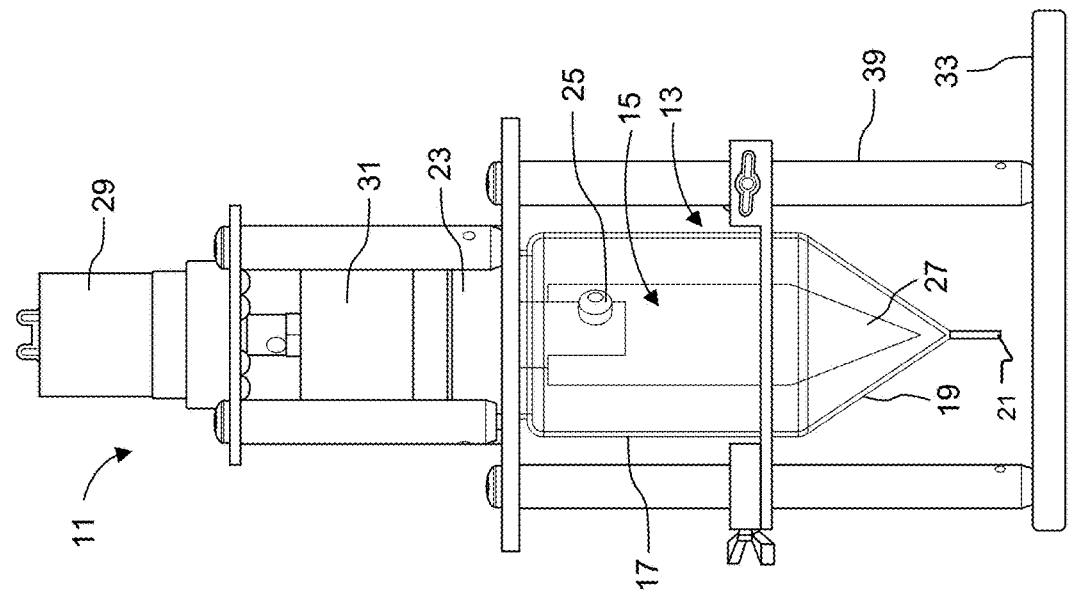
FIG. 2A is a schematic diagram of an agitator apparatus that can be used to prevent cells from settling while being kept in an incubator.
Figure 2D:
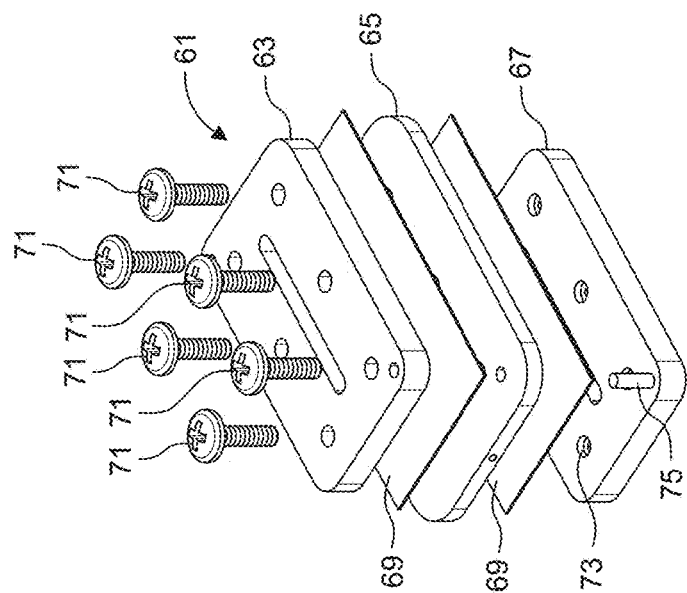
FIG. 2D is an exploded view of a fluidic capacitor that can be used in the system of FIG. 1.
Figure 2E:
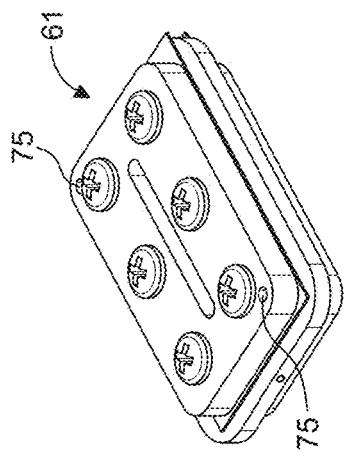
FIG. 2E is a perspective view of the assembled fluidic capacitor of FIG. 2D.
Figure 2C:
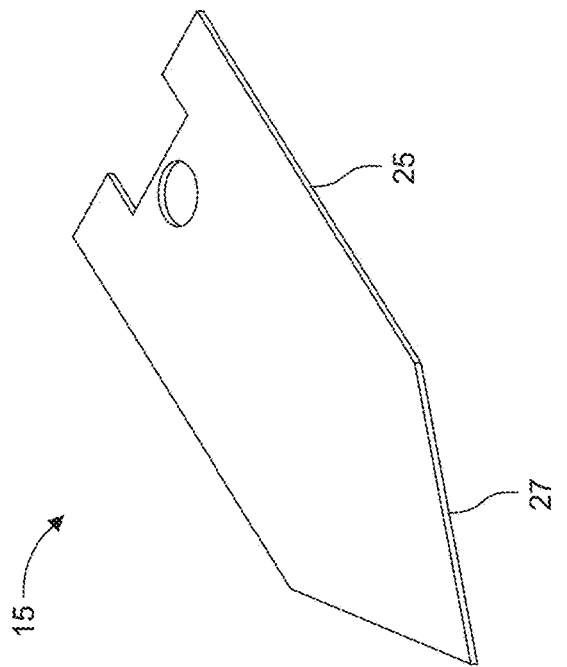
FIG. 2C is a perspective view of an impeller that can be used in the agitator apparatus of FIG. 2A.

In many cases, selecting a suitable impeller design takes into consideration the need to protect the cells from excessive shear forces in the cell reservoir while promoting sufficient agitation to reduce, minimize or entirely prevent their sinking to the bottom of the cell reservoir. In the specific embodiment of FIGS. 2A and 2B, impeller 15 has a profile that is similar to that of the cell reservoir 13 and includes an upper section 25 and a tapered lower section 27, as illustrated in FIG. 2C. In the embodiment of FIG. 2C, the impeller is a thin, flat structure configured to fit inside cell reservoir 13. The degree of taper, the relative length of sections 25 and 27 as well as other parameters can be optimized experimentally. Furthermore, other types of impellers can be employed.

Impeller 15 is connected to motor 29 via magnetic coupling 31.

The motor, magnetic coupling and the cell reservoir can be installed on a platform 33, which, in some implementations, is fabricated from aluminum breadboard. Cell reservoir 13 is stabilized by stabilization plate 35, while holder plate 37 holds the cell reservoir 13 at lid 23. Holder plate 37 can have a U-shape opening, e.g., for loading and unloading the cell reservoir and keeping it stable during agitation. Stabilization plate 35 and holder plate 37 can be mounted on platform 33 using pillar posts or other suitable means. In the embodiment of FIGS. 2A and 2B, apparatus 11 includes 3 male female pillar posts 39, which can be 6 inches long.

Motor subassembly 41, which can include 3 screws 43, is mounted on holder plate 37 using, for example, male female pillar posts 45, which can be 3 inches long. The motor spins a magnet that magnetically couples to the impeller, causing it to spin in the cell reservoir without direct contact.

Parameters for operating impeller 15 take into consideration the need to protect cells from excessive shear, while keeping the cells from sinking and settling at the bottom of the cell reservoir. In specific implementations, impeller 15 is operated at 160 rotations per minute, and imparts a maximum shear stress of about 2 dyne/cm$^2$ to the cells. It is important that shear stress remain below about 10 dyne/cm$^2$.

If a peristaltic pump is used to drive fluid out from outlet 21, a compliant structure can be placed in line to dampen flow oscillations created by the pump, providing a smooth flow to upstream devices. The compliant structure can be, for example, a fluidic capacitor, i.e. a microchannel with a floor and/or ceiling fabricated from a compliant material such as a polymer membrane that deforms in response to fluid pressure. An example is shown in FIGS. 2D (an exploded view of the fluidic capacitor 61) and 2E (a view of the assembled fluidic capacitor). As seen in these drawings, the fluidic capacitor 61 includes top (ceiling) plate 63, middle plate 65 and bottom (floor) plate 67, separated by two polymer membranes, namely sheets 69, which can be fabricated, for example, from high purity, high temperature silicone rubber or another suitable material. Top plate 63, first sheet 69, middle plate 65, second sheet 69 and bottom plate 67 are held together by screws 71 that can be threaded into threaded holes 73. Other arrangements for clamping together the plates and sheets can be employed. Ports 75 provide fluidic communication between, to and from other system components. In one example, outlet 21 (FIGS. 2A and 2B) is connected to a first (inlet) port 75, while the second (outlet port 75 is connected to pump 30 (FIG. 1).

Figure 2F:
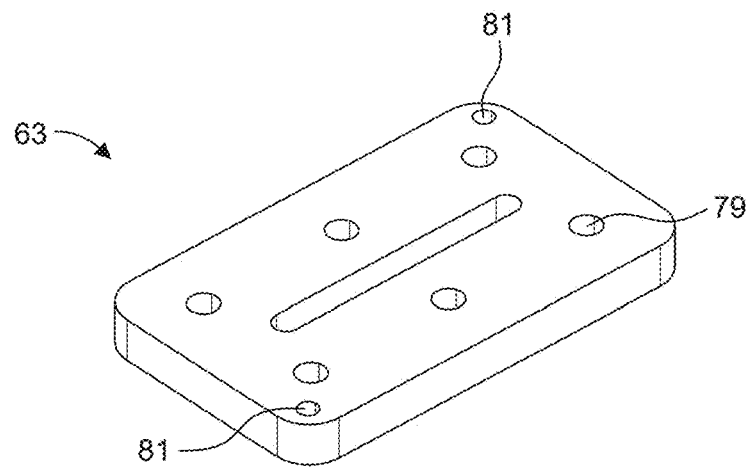
FIGS. 2F, 2G and 2H are perspective views of plate components of the fluidic capacitor of FIGS. 2D and 2E.
Figure 2G:
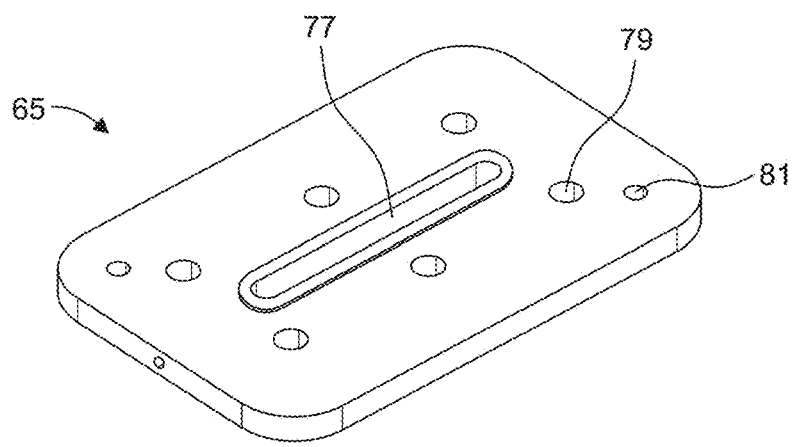
Figure 2H:
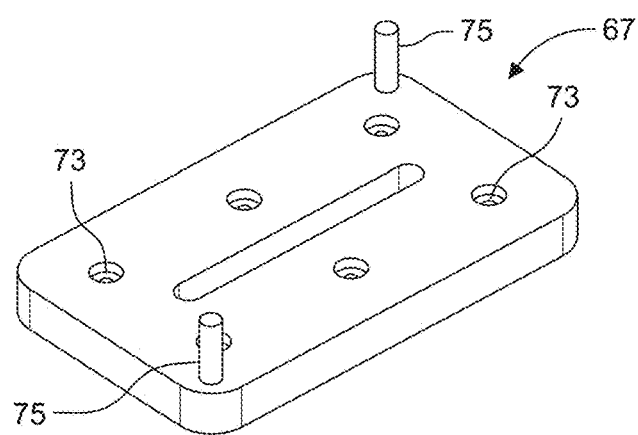

FIGS. 2F, 2G and 2H show, respectively, plates 63, 65 and 67. In more detail, a microchannel 77 is cut through the middle plate 65. Through holes 79 accommodate screws 71 while through holes 81 are configured to fit inlet/outlet ports 75.

During operation, fluid flowing through microchannel 77 is sandwiched between sheets 69, which are pliant and can accommodate volume fluctuations to smooth out the flow.

Figure 3:
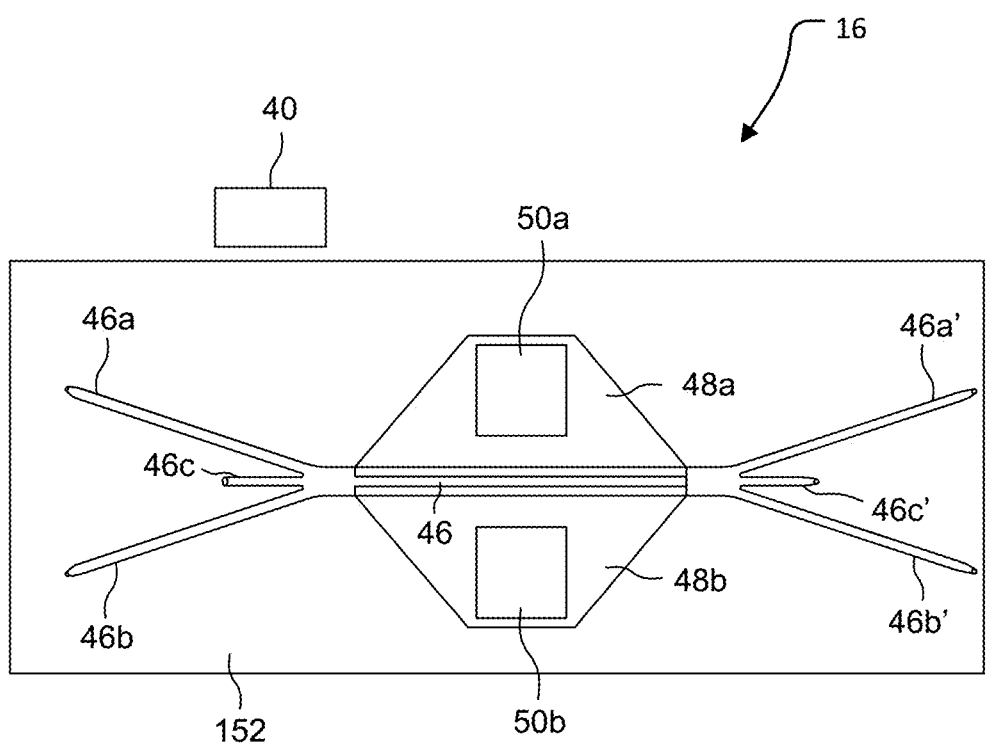
FIG. 3 is a top view showing a device component configured to support a flow arrangement that uses a central stream and side streams.

FIG. 3 is a top view of an exemplary electroporation assembly 16 that can support a sheath flow configuration such as described above. The arrangement includes microfluidic center channel 46 having trifurcating inlets (elements 46a, 46b and 46c) and trifurcating outlets (elements 46a', 46b' and 46c') in FIG. 3.

Microfluidic channel 46 can be fabricated in a substrate 52 such as hard plastic (which, for many materials, renders the device disposable). Examples include but are not limited to cyclic olefin copolymer (COC) thermoplastic, a polyimide film, such as Kapton®, polystyrene, PEI (polyetherimide), e.g., Ultem®, or a combination of various polymers. Other materials such as glass, quartz, silicon, suitable ceramics, and so forth also can be employed.

The channel dimensions can range from 500 micrometer (μm) to 3 millimeter (mm) in width, 1 centimeter (cm) to 5 cm in length, and 125 μm to 500 μm in height. A pair of coplanar rhomboid-shaped electrodes (48a and 48b) are patterned onto the polymer layer beneath the floor of the microchannel with square wire bond or solder pad areas defined by cutouts in the polymer layers that expose the electrodes for external access. A masking layer is placed between the electrode layer and the microfluidic channel 46, with cutouts that define the portion of electrode that is exposed to fluid in the microchannel. Typically, the electrodes are formed from an electrochemically stable material, such as platinum metal (Pt). The portion of the electrodes that are exposed to the fluid in the channel have dimensions of 100-250 μm in width and 8-45 mm in length and interface to the electrical function generator 40 via connection to the square soldering pads (elements 50a and 50b in FIG. 3).

In an arrangement such as that of FIG. 3, the relative flow rates of the center vs. side streams can be tuned. In one example, the relative flow is adjusted so that the electrodes only make contact with the side streams. The total flow rate can range from 375 μL/min to 6 ml/min. In specific examples, the flow ratio for the side streams vs. the center stream is typically in the range of 1:0.5 to 1:1 (single side:center). When the conductivity of the solution comprising the center stream is much lower than the conductivities of the solutions comprising the side streams (e.g., 10× or more), the center stream dominates the electrical resistance of the circuit, such that, when voltage is applied to the electrodes, most of the voltage is dropped across the center stream.

The voltage (from the electrical function generator 40 in FIG. 1) is applied across the square soldering pads 50a and 50b and may take the form of sinusoids with periods ranging from 10 nanoseconds (ns) to 10 milliseconds (ms), or pulse trains with pulse widths ranging from 10 ns to 10 ms. The magnitude of the applied voltage can vary, so as to generate an electric field across the center stream that ranges from about 2-1000 kV/m, and pulse widths ranging from 10 ns to 10 ms. The frequency of the pulse train can be varied as well, and ranges, for example, from one pulse per cell residence time, to 10 pulses per residence time or more.

An arrangement such as that in FIG. 3 can support the use of different buffers. In specific embodiments, the sheath side streams are characterized by high electrical conductivity (σ), e.g., in the range of from about 1 to about 2 Siemens per meter (S/m), while the central sheath stream has a low σ, e.g., within a range of from 10 to 1000 micro Siemens per centimeter (μS/cm). This approach is compatible with the use of buffers suitable for cell culture and/or buffers suitable for electroporation.

Thus, in one implementation, the cells, in their preferred buffer, are provided via the center sheath stream 46c. The two side streams 46a and 46b are supplied from the high conductivity media reservoir 24 by pump 34 in FIG. 1. It is common for such a cell preferred buffer to have a high σ, e.g., in the range of from about 10,000 to about 20,000 (μS/cm).

Low σ electroporation buffer flows in central stream 46c and is supplied from electroporation reservoir 22 by pump 32 in FIG. 1.

Figure 4A:
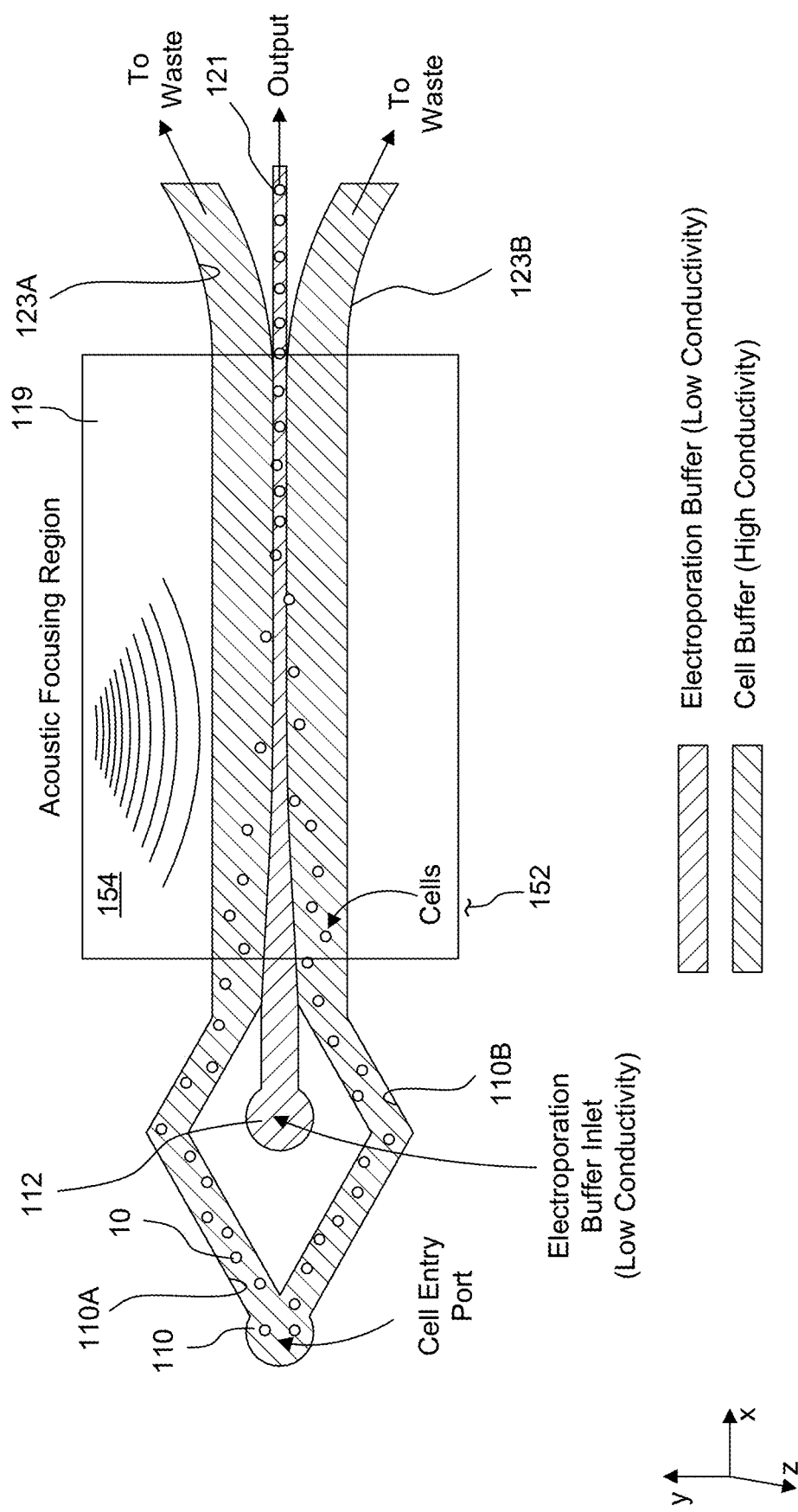
FIG. 4A is a schematic view of an acoustically-driven, rapid buffer exchange arrangement that can be used for the electroporation of cells.

Prior to entering the electroporation module 16 (FIG. 3), cells coming from incubator 12 are flowed into the side stream port 110 of an acoustic media exchange module of FIG. 4A where they are driven or pushed, e.g., acoustically, from the high conductivity side sheath streams to the center stream, which contains a low σ electroporation buffer and cargo. As a result, the cells become suspended in the central, electroporation buffer (which is then delivered to the center stream port 46c of module 16). The acoustic energy to drive the cells from one buffer to another is supplied from the acoustic function generator 42 to an acoustic transducer 154 attached to the channel substrate 152.

After the electroporation operation (conducted in electroporation assembly 16 in FIGS. 1 and 3), cargo-containing product cells can remain suspended in the central stream and can be collected from outlet 46c'. Fluid obtained from outlets 46a' and 46b' is handled as waste or recycled. In other embodiments, a second buffer exchange (see buffer exchanger 18 in FIG. 1) can be performed to move the cargo-containing product cells from the low σ electroporation buffer in the central stream to the high σ fluid in the side streams. In this configuration, cargo-containing product cells can be collected from outlets 46a' and 46b'. Fluid from outlet 46c' is handled as waste or directed to a collection arrangement for reuse.

Schematically shown in FIG. 4A is one arrangement of the (first) buffer exchanger 14 for moving cells from sheath streams containing high conductivity cell buffer, to a low conductivity electroporation buffer flowing in the central stream. Cells in their preferred medium, i.e., cell buffer, are introduced through the cell inlet 110. The stream is supplied from the incubator 12 by the pump 30. The medium input into the inlet is bifurcated into two cell subchannels 110A, 110B. The cell subchannels 110A, 110B diverge from each other in the y-axis direction and then converge as they progress in the positive x-axis direction. The cells are acoustically driven from the sheath cell buffer streams into the central electroporation buffer stream in the acoustic focusing region 119. The electroporation buffer is supplied from the electroporation buffer reservoir 22 by pump 32. The acoustic energy is supplied from the acoustic function generator 42 to an acoustic transducer 154 attached to the channel substrate 152. Output cells are collected from the central outlet 121, while the cell buffer is collected at outlets 123A and 123B as waste or directed to a collection arrangement for reuse. As discussed previously, in one configuration, the output cells from outlet 121 are supplied to center sheath stream 46c of the electroporation module 16 of FIG. 3.

Figure 4B:
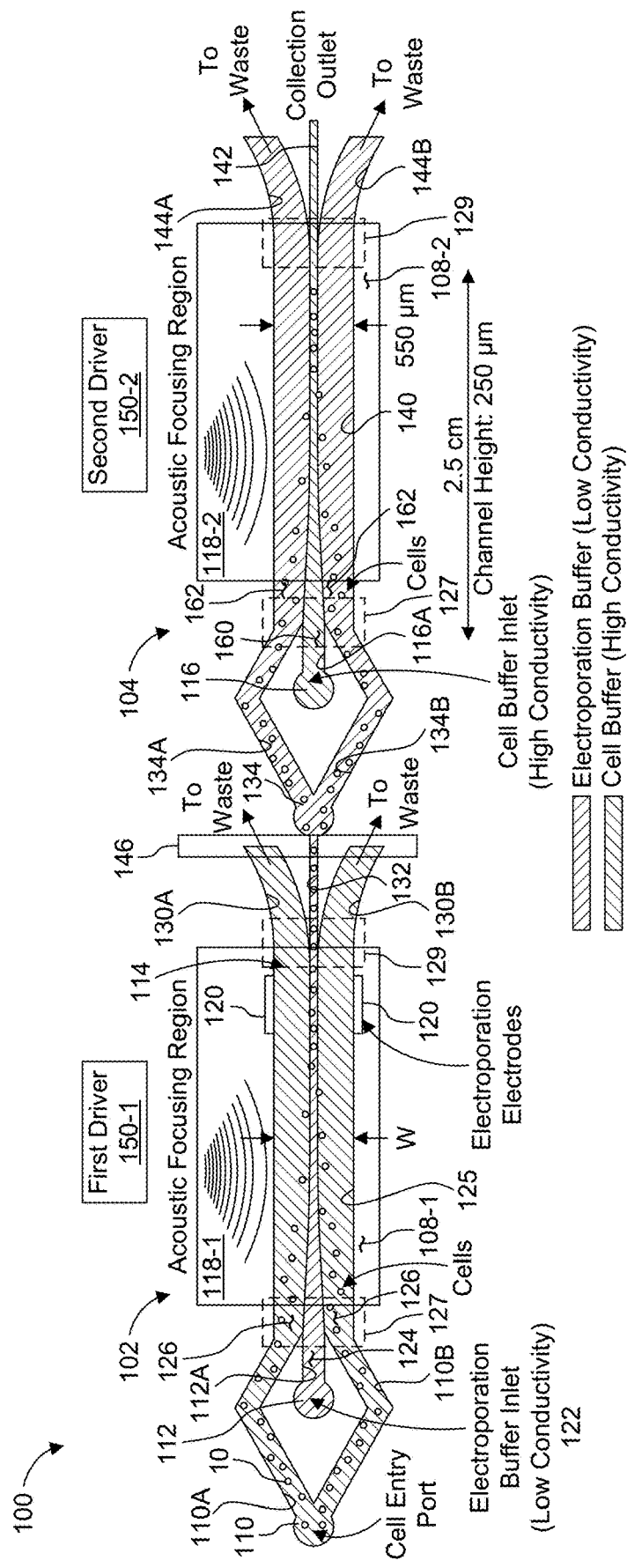
FIGS. 4B, 4C and 4D are schematic views of acoustically-driven, rapid buffer exchange and electroporation arrangements.

FIG. 4B shows a two-stage, acoustically-driven, rapid buffer exchange system 100 used for electroporation of cells, which performs the functions of the first buffer exchanger 14, electroporation assembly 16, and the second buffer exchanger 18 described in FIG. 1.

This example comprises two or more connected microchannels 102, 104. Typically, the channels are fabricated from a hard polymer substrate or substrates 108, such as polystyrene, or other hard substrates such as silicon, glass, and quartz. The prototypical two-channel system is described here, but additional channels can be added in kind.

In the illustrated example, each of the microchannels 102, 104 is fabricated in a separate substrate 108-1, 108-2.

Each microchannel 102, 104 supports a sheath or co-flow, with a center stream 124 and streams 126 on either side. In specific examples, the center stream 124 has a composition that is different from the composition of the side streams 126. Flow is maintained in the laminar regime, so mixing between the streams is minimal.

In order to maintain this laminar flow, the fluid velocities of the center stream 124 and the sheath or side streams 126 are such that the Reynolds number, Re, in the system is small (Re<<~2000) in the region of the trifurcated inlets in convergence region 127. Preferably, Re is less than 500 and is preferably less than 10.

The microchannels 102, 104 may be rectangular in cross section with width and height dimensions that range from 100 micrometers (μm) to 1000 μm. The length of each of the microchannels 102, 104 ranges from 5 millimeters (mm) to 30 mm.

Other embodiments are possible, however. Another example has a concentric flow geometry wherein the sheath stream 126 surrounds the center stream 124 on all sides. Particles, such as cells 10, initially introduced into the one or more sheath streams 126, e.g., at an input region such as inlet port 110, can range in diameter from 100 nanometers (nm) to 25 μm. For example, T-cells, a typical particle for electroporation transfection, range in size from about 6 μm to 12 μm.

In one application, the system 100 is used to rapidly move cells into and out of a specialized electroporation buffer, each microchannel has two inlets 110, 112 and a trifurcating outlet 114. Electroporation buffer is introduced directly into the first microchannel 102 through inlet 112 and forms or comprises the center stream. The electroporation buffer is supplied from the electroporation buffer reservoir 22 by pump 32 in FIG. 1. Cells in their preferred media, i.e., cell buffer, are introduced through the cell inlet 110. The cells are supplied from the incubator 12 by the pump 30. The media input into the inlet is bifurcated into two cell subchannels 110A, 110B. The cell sub channels 110A, 110B diverge from each other in the y-axis direction and then converge as they progress in the positive x-axis direction.

The cell buffer and the electroporation buffer generally differ from each other in terms of how long the cells can survive in the respective buffers. An example of a cell buffer for T cells would be TexMACS (sold by Miltenyi Biotec Inc.) or RPMI (sold by Thermo Fisher Scientific Inc.). Such cell buffer typically contains physiological salt concentrations that match cell osmolarity and nutrients. On the other hand, an example of an electroporation buffer would be BTX low-conductivity buffer (sold by BTX). Such electroporation buffer typically has lower salt concentration to reduce the conductivity but has added sugars to reduce osmotic shock to the cells.

The cell sub channels 110A, 110B converge toward each other, on either side of an electroporation buffer flowing from subchannel 112A to create a trifurcated inlet in the convergence region 127. In this way, all three subchannels 110A, 110B, 112A deliver their flow into a switching channel 125. The flow of streams 126, containing the cells, converges around the center stream 124 as two side sheath streams of the flow.

At the other distal end of the first microchannel 102, the switching channel 125 delivers flow to two side outlet subchannels 130A, 130B in divergence region 129. Here, the subchannels 130A, 130B diverge from each other in the y-axis direction as they progress in the x-axis direction and also diverge from a center outlet subchannel 132. The two side outlet subchannels 130A, 130B carry flow largely from the original sheath input streams 126 and exit as waste or are collected for reuse.

The center outlet subchannel 132 carries flow from the center stream of the switching channel. It contains the cells 10 in the electroporation buffer.

Here, also laminar flow is preferably maintained. The fluid velocities within a divergence region 129 are such that the Reynolds number, Re, in the system is small (Re<<~2000) in the region of the trifurcated outlets in divergence region 129. Preferably, Re is less than 500 and is preferably less than 10.

The center outlet subchannel 132 of the first microchannel 102 directs flow to inlet 134 of the second microchannel 104, preferably fabricated in a separate substrate 108-2. The second microchannel inlet 134 bifurcates into two cell subchannels 134A, 134B. The cell sub channels 134A, 134B diverge from each other in the y-axis direction and then reconverge as they progress in the positive x-axis direction.

The cells' preferred media or a secondary media (possibly containing a different biomarker or cargo to be transfected) is introduced into the other inlet 116 of the second microchannel 104. This media is supplied from the cell media reservoir 26 by the pump 36 in FIG. 1. The electroporated cell sub channels 134A, 134B converge toward each other, on either side of a cell buffer subchannel 116A, which carries the flowing media in the positive x-axis direction.

The electroporated cell sub channels 134A, 134B and the cell buffer subchannel 116A deliver their flow into a second switching channel 140. Here, the cells 10 are directed, from the side streams 162, to the center stream 160 of the second switching channel 140 of the second microchannel 104. As before, the Reynolds number, Re, is small (Re<<~2000) in the region of the trifurcated inlets in convergence region 127. Preferably, Re is less than 500 and is preferably less than 10.

Cells can be collected from the center outlet subchannel 142 of the second microchannel 104. The collected cells from the microchannel 142 are transferred to the incubator 20 shown in FIG. 1. Two lateral outlet subchannels 144A, 144B, at the end of the switching channel 140 and on either side of the center outlet subchannel 142, carry fluid to waste or a collection arrangement for reuse.

Alternatively, cells can be directed toward an additional microchannel and so forth, depending on the number of buffer exchanges that are desired. Typical input flow rates range from 1 microliter per minute (μl/min) to 1 milliliter per minute (ml/min).

In one example, the substrates 108-1, 108-2 are bonded to separate lead zirconate titanate piezoelectric transducers 118-1, 118-2 using cyanoacrylate adhesive, and it is shorter than the microchannel. The transducers 118-1, 118-2 are connected to and driven by separate drivers 150-1, 150-2 of the acoustic function generator 42 shown in FIG. 1, each of which includes a radio frequency amplifier which is driven by a function generator that creates the sinusoidal signal which excites the respective channel 102, 104. This device configuration has been shown to support an acoustic resonance frequency between 900 to 990 kHz, where a stable standing pressure wave is generated across the width of each of the switching channels 125, 140. The transducers and microchannel substrates are also preferably mounted to aluminum plates which acts as a heat sink. A thermoelectric cooler (TEC) element and base plate sit beneath the aluminum plate. A thermistor is connected on top of the transducer near the microchannel, which is connected to a TEC controller along with the TEC, to make a closed-loop temperature control system. The temperature is preferably held at approximately 26° C.

An acoustic isolator 146 prevents acoustic energy from each of the acoustic transducers 118-1, 118-2 from affecting the other microchannel. This prevents cross-talk between the two microchannels and allows them to be separately driven and tuned. In the present example, isolation is achieved by fabricating the microchannels 102, 104 in separate substrates 108-1, 108-2 and then connecting the substrates with flexible tubing to avoid acoustic crosstalk.

These transducers 118-1, 118-2 are actuated by separate drivers 150-1, 150-2 of the acoustic function generator 42 of FIG. 1. Each of these drivers applies a separately tunable sinusoidally varying voltage, for example. The frequency is chosen such that a stable standing pressure wave is generated across the width of each switching channel 125, 140 of the respective microchannel 102, 104 (transverse to the fluid flow direction). In this way, the transducers 118-1, 118-2 drive the operation of the (first) buffer exchanger 14 (FIG. 1) and second buffer exchanger 18 (FIG. 1), respectively, in the two-stage, acoustically-driven, rapid buffer exchange system 100 of FIG. 4B.

For the fundamental focusing mode there is a single pressure node in the fluid. The acoustic radiation pressure exerts a force on the cells in the direction of the pressure node. This results in the migration of cells out of the side streams and into the center stream, toward the centerline of the cross-section of the channel. In the first microchannel 102, this action results in cells moving out of their preferred buffer and into the electroporation buffer, where they are electroporated. In the second microchannel 104, this action results in cells moving out of the electroporation buffer and back into their preferred or a new buffer. This results in a residence time of cells in the electroporation buffer of seconds or less.

A pair of electroporation electrodes 120 drive the operation of the electroporation assembly 16 (FIG. 1) in the two-stage, acoustically-driven, rapid buffer exchange system 100 of FIG. 4B. The electroporation electrodes 120 can be positioned in the region between the trifurcated inlet and trifurcating outlet of the first microchannel 102; for example, halfway between the trifurcation inlet and trifurcation outlet. If multiple stages of electroporation, with multiple sequential payloads being required, electrodes may also be fabricated in the 2nd and any additional microchannels, so long as the final microchannel returns cells to their preferred buffer. The electrodes 120 are placed such that cells pass through the electroporation field after being focused into the electroporation buffer in the center stream 124 of in the switching channel 125. The electrodes are driven by the electrical function generator 40 shown in FIG. 1.

The electrodes 120 may be patterned using photolithographic processes onto the floor and ceiling of the switching channel 125, or onto the sidewalls of the channel 125. Electrode area (especially the dimension along the flow axis (x-axis direction in FIG. 4B) of the channel) and flow rate determine the residence time of cells in the electric field. Chosen residence times can vary from 100 microseconds (is) to about a second. Alternatively, "remote electrodes" can be used, comprising fluidic connections from open ports to the main channel, and wire electrodes placed in the ports (such a configuration requires Faradaic current to pass through the electrodes). An AC (for example, sinusoids or pulse trains with periods/pulse widths ranging from 10 ns to 100 s of microseconds) or a DC electric field is established and remains active while cells flow through the device. The magnitude of the field is tuned for the specific cell type to a value sufficient to achieve permeabilization, and is typically in the range of 2-200 kV/m.

Cargo can be mixed into either the electroporation buffer introduced into the first microchannel 102 at inlet 112, or with the cells in the preferred cell buffer that is introduced into the cell inlet 110. The former enables tuning of the cells' exposure times to the cargo by adjusting the timing of transit into the second microchannel.

In some embodiments, the individual microchannels are fabricated separately, connected fluidically by polymer tubing, and are acoustically-actuated independently. The individual microchannels might even be fabricated on the same substrate and actuated together using a single piezoelectric transducer. In some embodiments the "waste" streams in the two side outlet subchannels 130A, 130B from the first microchannel 102, containing the cells' preferred media, are directed and coupled into the center stream via inlet 116 of the second microchannel 104 (instead of a second pump delivering media directly into the center stream of the second microchannel). In some embodiments, multiple sequential microchannel setups are laid out in parallel with manifolds for introducing cells and buffer, increasing throughput.

Figure 4C:
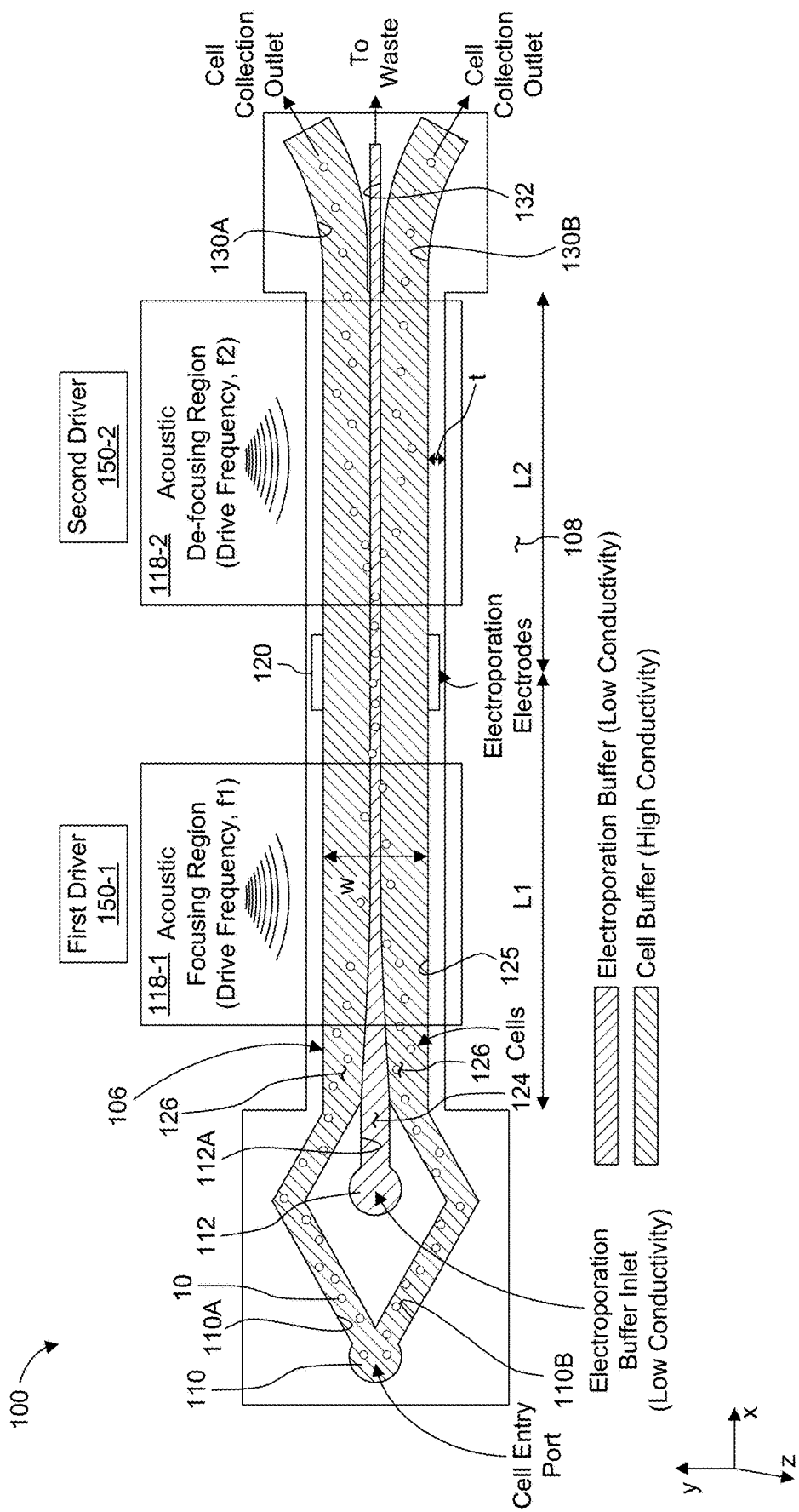
Figure 4D:
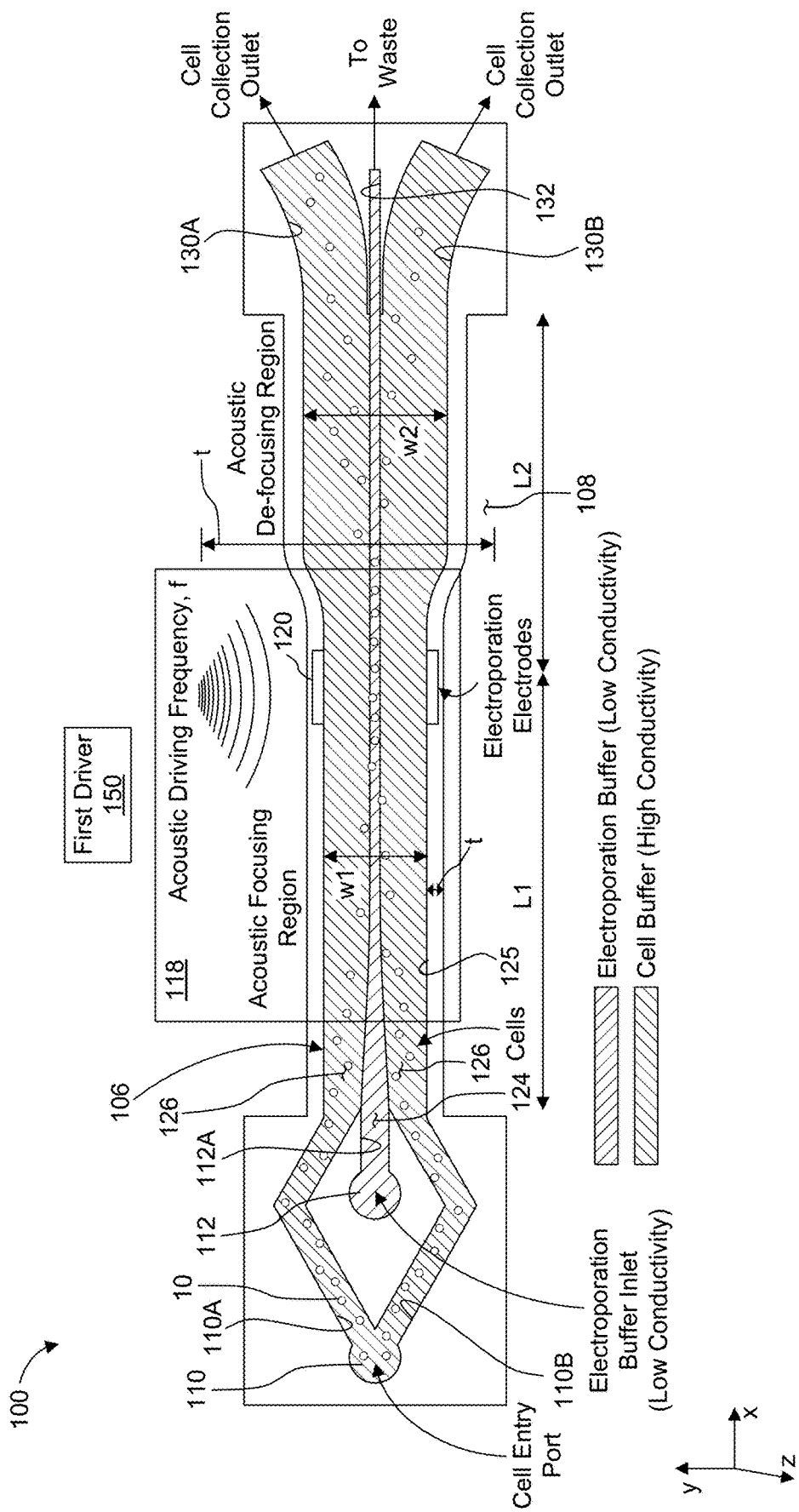

FIGS. 4C and 4D show two alternate embodiments of the rapid buffer exchange system 100. Here, in a compound microchannel 106, the cells are focused into the center stream for electroporation, and then focused back into the outer stream (called "de-focused" here) for collection.

In more detail, electroporation buffer (supplied from electroporation buffer reservoir 22 by pump 32 in FIG. 1) is introduced directly into the compound microchannel 106 through inlet 112 and comprises the center stream of the sheath flow, as shown in FIG. 4C. Cells in their preferred media (supplied from incubator 20 by pump 30 in FIG. 1) are introduced through the cell inlet 110. The media input into the inlet is bifurcated into two cell subchannels 110A, 110B. The cell sub channels 110A, 110B diverge from each other in the y-axis direction and then converge as they progress in the positive x-axis direction.

The cell sub channels 110A, 110B converge toward each other, on either side of an electroporation buffer subchannel 112A to create a trifurcated inlet. In this way, the subchannels 110A, 110B, 112A deliver their flow into a compound switching channel 125. The flow 126, containing the cells, converges around the center stream 124 as two side sheath streams of the flow as in previous embodiments.

At the other distal end of the first microchannel 102, the switching channel 125 delivers flow to two side outlet subchannels 130A, 130B, which diverge from each other in the y-axis direction as they progress in the x-axis direction. The two sided outlet subchannels 130A, 130B carry flow largely from the original sheath streams 126, but in this example, the cells have been moved into the sheath streams 126 upstream of the side outlet subchannels 130A, 130B.

The long compound switching channel 125 is divided into two regions by a set of electroporation electrodes 120 on either lateral side of the channel at a distance L1, measured along the x-axis, from the trifurcating inlet, which distance, for example, can range from 20 to 40 mm. The channel has a width of w, which can range from 420 to 740 µm. Acoustic actuation at frequency, f1, which typically ranges from 400 to 1000 kHz, is provided by acoustic function generator 42 in FIG. 1, and applied by the first driver 150-1 to the first acoustic wave transducers 118-1 and is used to drive cells to the center, low-conductivity stream upstream of the electroporation electrodes 120. In the region downstream of the electrodes 120, a different frequency, f2, typically greater than f1, by a factor of 1.5 to 2.5, for example (provided by a second acoustic function generator, e.g., similar to acoustic function generator 42 in FIG. 1) is applied by the second driver 150-2 to the second acoustic wave transducers 118-2, which is used to drive the cells out of the center stream.

The center outlet subchannel 132 at the distal end of the microchannel 102 carries flow from the center stream of the switching channel, e.g., to waste or recycling.

In FIG. 4C, a single acoustic driving frequency is used, but the channel downstream of the electrodes 120 is wider, having a width w2 that is greater than w1 (the width upstream of electrodes 120) by a factor of 1.5 to 2.5. This alters the nodal structure of the soundwaves in the channel and achieves the similar forcing of the cells to the side streams.

In both the embodiments of FIGS. 4C and 4D, the width t of the substrate 108 with respect to the width of the fluid channel w, w1, w2 is an important parameter. It ranges from 550 to 1050 µm.

In still a further embodiment, the microchannel(s) continue to sit atop a piezoelectric transducer (or surface acoustic wave transducer) for generating the acoustic standing mode which acts on the microparticles (or cells) in the microchannel(s). However, this embodiment does not employ a set of electroporation electrodes for generating electric fields in the fluid. Such a configuration, i.e., without electroporation electrodes, is useful for "washing" cells or for transferring them from one media to another, for example. It can represent a good alternative to the conventional method that involves spinning down the microparticles (cells) in a centrifuge, removing the supernatant, adding the second buffer, and resuspending the microparticles.

Shown in FIGS. 5A and 5B are microscopy images demonstrating acoustically-driven rapid buffer exchange. When the acoustics are off (FIG. 5A), cells in the side streams pass through without being deflected and remain in their buffer. When the acoustics are activated (FIG. 5B), cells are deflected from the side streams into the center stream, which can include a different buffer or contain different reagents.

In some embodiments of the invention, the system illustrated in FIG. 1 employs an electroporation assembly 16 that consists essentially of or comprises at least one microchannel arrangement (device) such as that shown in FIG. 3.

An electroporation assembly also can include two or more (i.e., multiple or a plurality of) electroporation arrangements in a parallel configuration as further described below. Such an assembly can be used not only in the high throughput, high efficiency continuous flow systems illustrated in FIG. 1, but also in other systems or independently, as flow electroporation devices for transfection of cells (or other targets such as exosomes, etc.) that have been loaded into an appropriate, low-conductivity, electroporation buffer using conventional means (e.g., centrifugation and resuspension). In this configuration, transfected cells are collected at the output and returned to incubation or storage conditions manually. Further implementations utilize the electroporation assembly with parallel channels in systems that do not employ acoustically-driven buffer exchanges.

Figure 6:
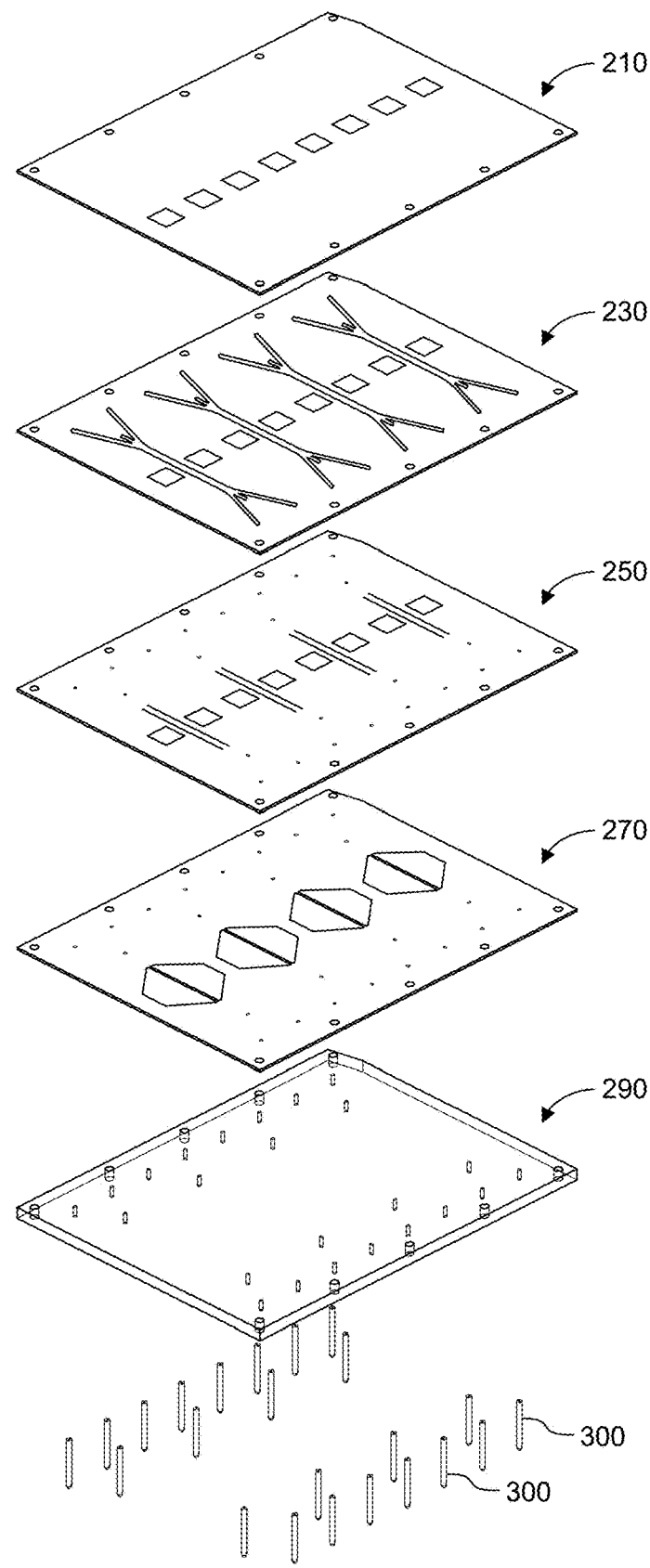
FIG. 6 is an exploded view of components in an electroporation assembly.
Figure 7:
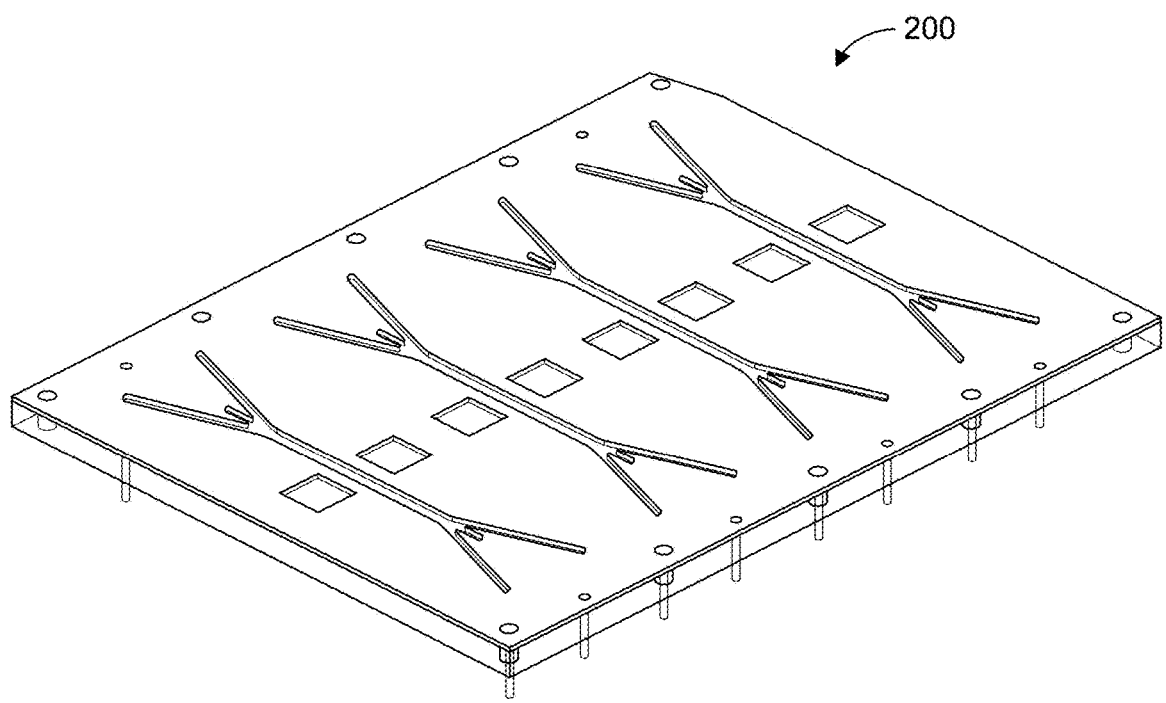
FIGS. 7 and 8 are perspective views of an electroporation assembly that includes the components shown in FIG. 6.
Figure 8:
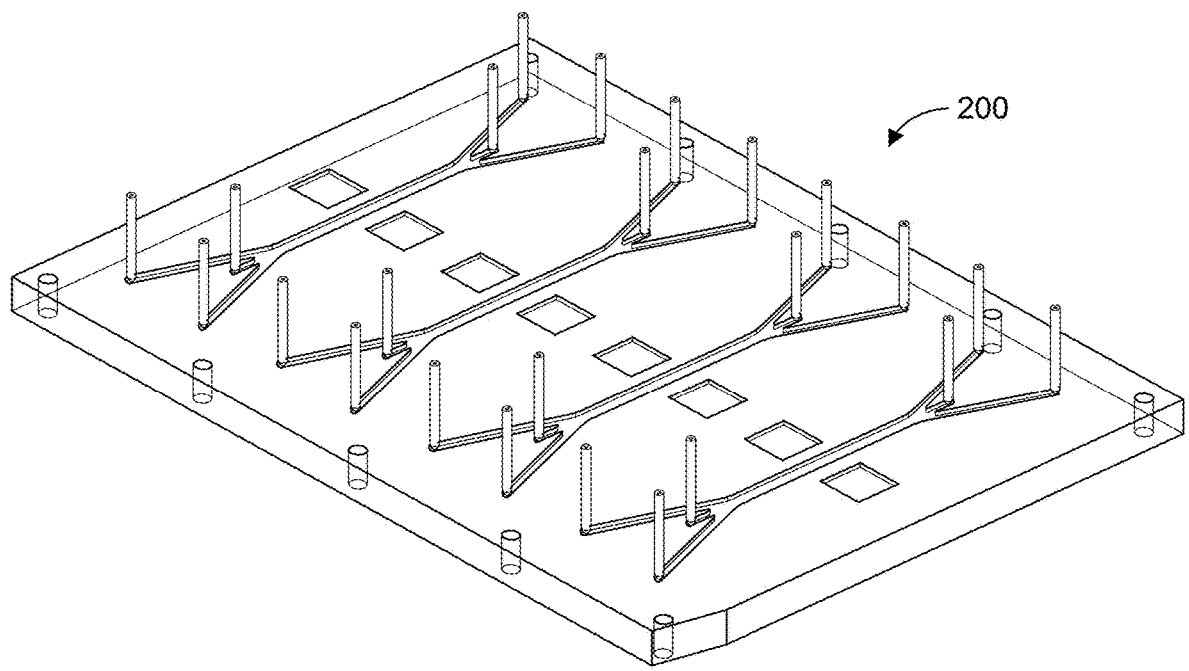

FIG. 6 is an exploded view of assembly 200 which includes several layers or plates (namely layers 210, 230, 250, 270 and 290) further described in FIGS. 8-12. The layers can be laminated in a stacked configuration as shown in FIGS. 7 (top view) and 8 (bottom view). In one implementation, the laminate is prepared by curing a suitable adhesive film disposed between adjacent plates.

Figure 9:
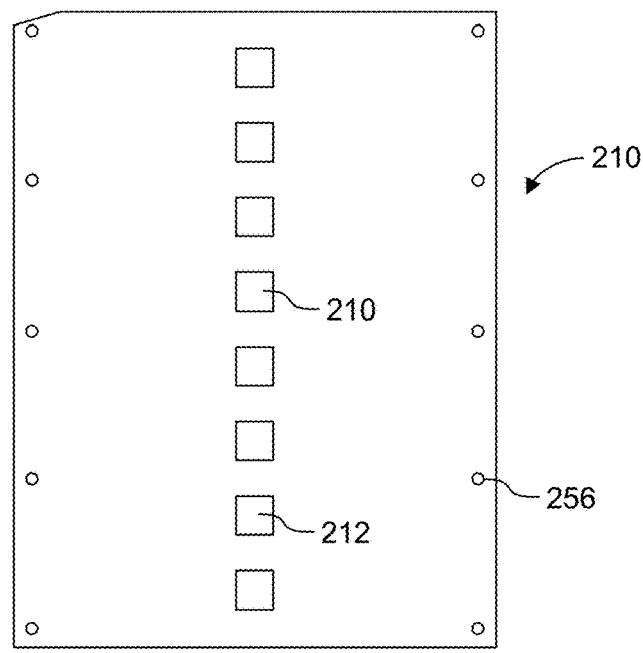
FIGS. 9 through 13 are top views of the components in FIGS. 6-8.

Turning to the individual layers, shown in FIG. 9 is viewing layer 210 which includes openings 212 that provide access for solder bonding to the electrodes (48a and 48b) and can have a thickness of 10 millimeters (mm or mil). In one example, layer 210 is made of Ultem® material.

Figure 10:
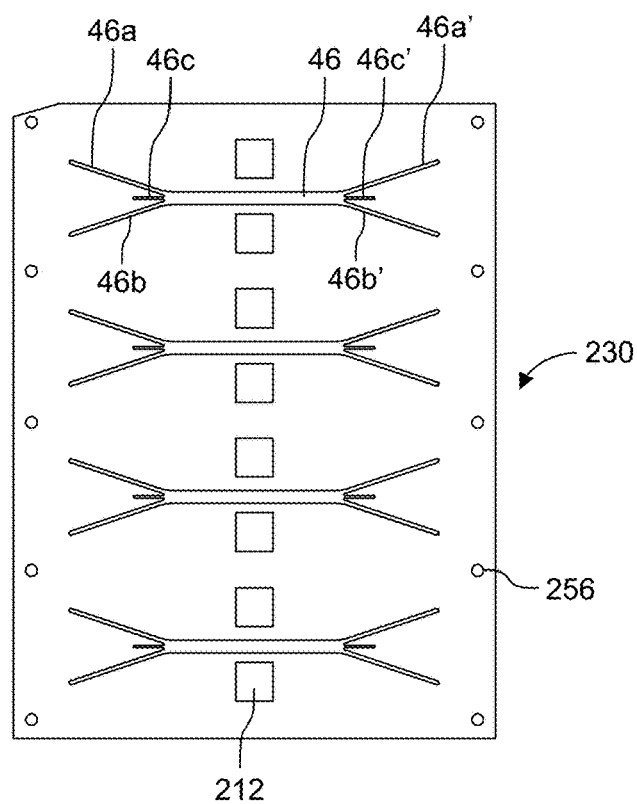

FIG. 10 shows fluidic channel layer 230 including a plurality (four being shown in the figure) of fluidic microchannels, each having the trifurcating inlets and outlets for a central and side streams and the microfluidic center channel 46, essentially as described with reference to FIG. 2B.

The specific embodiment described above has four parallel fluidic microchannels. In a preferred arrangement, these would be used in parallel to process cells from a single common incubator 12. The use of the parallel microchannels allows for higher throughput, such as higher than 4 million cells per minute.

In general, micro channels cannot be simply made wider since the electric fields are optimally placed across a few or even single cells. Thus, in further implementations, higher numbers of parallel fluidic microchannels are fabricated in a single assembly 200. One embodiment includes at least 10, 20, 30, 40, 50 or more fluidic microchannels that are operated in parallel between an input common incubator 12 to output modified cells to a common output incubator 20.

In more detail, each fluidic microchannel has trifurcating inlets 232a, 232b and 232c and trifurcating outlets 232a', 232b' and 232c'. Hypodermic stainless steel tubing (e.g., nominally 25 Gauge tubing, 0.4 inches long) inserted into these inlets/outlets and sealed with epoxy can serve as an interface to the device for introducing cells and fluids. Plastic tubing (e.g., 0.38 millimeter inner diameter, vinyl) can be press fit onto the stainless steel tubing. As seen in the figure, the fluidic microchannels are arranged in a parallel configuration. Fluidic channel plate 230 can have a thickness of about 10 mil and can be fabricated from Ultem®, for example.

Preferably, the channels, and especially the microfluidic center channel 46 are fabricated in the fluidic channel layer 230 by forming slots all the way through the layer. Different technologies can be used upon the slots. In the current implementation, the slots are formed with laser machining. Other options are mechanical milling and photolithographic processes, to list a few examples.

Figure 11:
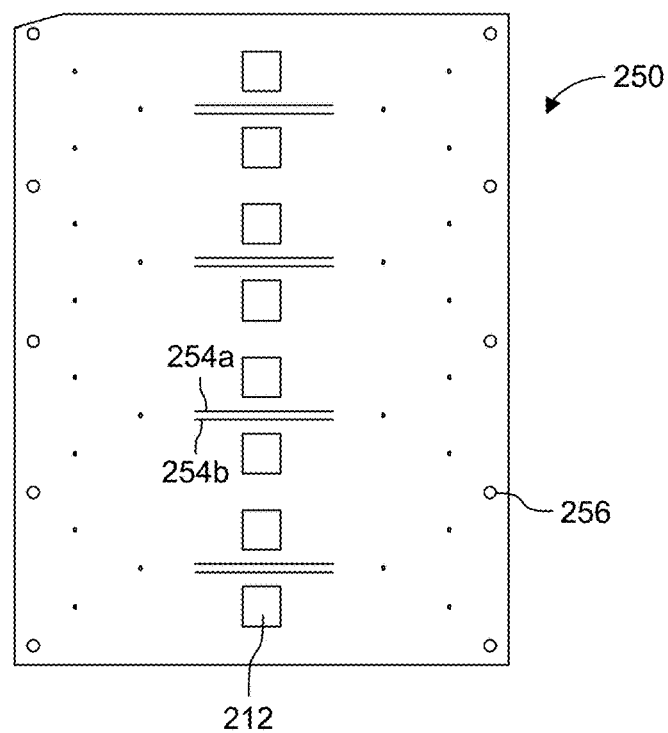

The layer shown in FIG. 11 is electrode frame 250, provided with electrode slots (or trenches) 254a and 254b. These slots are formed all the way through the electrode frame 250 using a fabrication technique as described earlier. The slots enable fluid communication between the proximal (long) edges of each of the rhomboid electrodes and the fluid in microfluidic center channel 46. The electrode frame can be made from Ultem® or Kapton®, with a thickness of about 1 mil, for instance. Holes 256 are provided for lamination alignment dowel pins.

Figure 12:
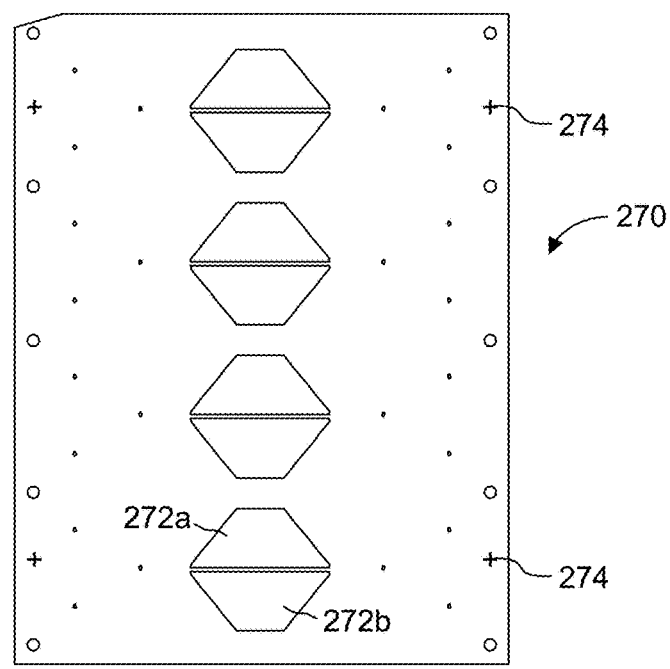

FIG. 12 shows electrode layer 270 including four pairs of rhomboid metalizations 272a and 272b that form the pairs of coplanar rhomboid electrodes (48a and 48b). The metalizations can be fabricated by the deposition (e.g., sputtering through a shadow mask) of an electrochemically stable material, platinum metal, for example, on an Ultem® film of 5 mil, for example. Fiducial markers 274 are provided for alignment of the deposition mask used in the fabrication of the electrode layer.

Figure 13:
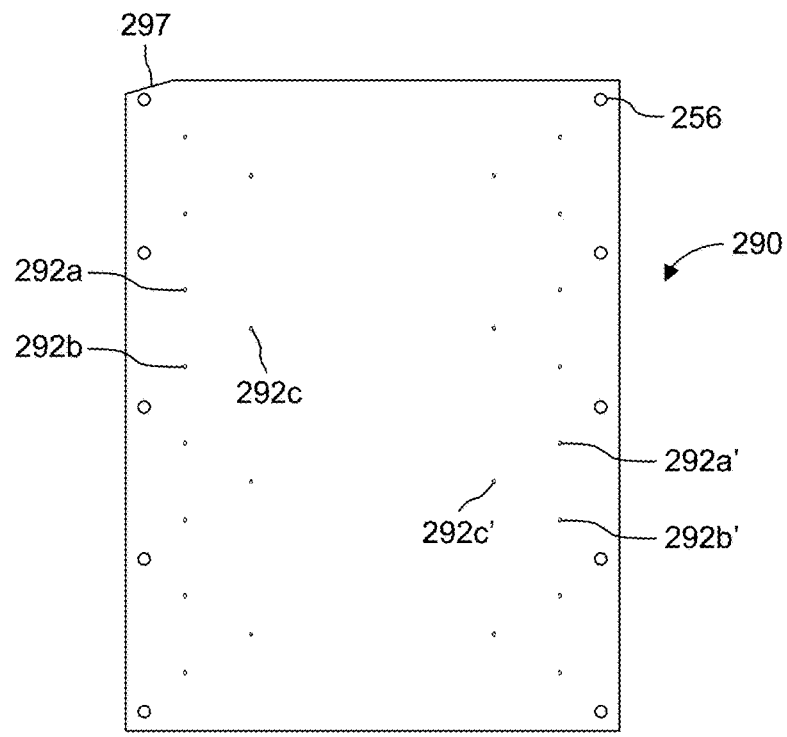

Shown in FIG. 13 is port plate 290, made, for example, from a 3/32" thick Ultem® material and provided with openings 292a, 292b and 292c, for access to the trifurcating inlets 46a, 46b and 46c (FIGS. 2B and 9), and openings 292a', 292b' and 292c' for access to trifurcated outlets 46a', 46b' and 46c' (FIGS. 2B and 10). These openings are sized to accommodate tubes 300 shown in FIG. 5. As described above, hypodermic stainless steel tubing (nominally 25 Gauge tubing, 0.4 inches long) can be inserted through these openings, connected to the inlets/outlets of the microchannels and sealed with epoxy to form an interface to the device for introducing cells and fluids. A suitable gauge plastic tubing can be press fit onto the stainless steel tubing.

For proper orientation during assembly and fabrication, plates 210, 230, 250, 270 and 290 can be marked by chamber 297. The plates are preferably adhered to each other. In one example, an adhesive film such as R/flex 1000 sheets is attached to some plates prior to laser machining. The adhesive sheets are then cured with high temperature and pressure, for example.

A system such as system 10 (FIG. 1), optionally including one or more of the subassemblies described above (e.g., with reference to FIGS. 2-4D and 6-13), can be operated as follows. A cell container, such as a blood bag, is introduced into the first incubator 12 and attached to an agitation mechanism that prevents the cells from settling due to sedimentation. Silastic tubing makes a fluidic connection between the blood bag and a first rapid buffer exchange module and a peristaltic pump 30 drives a flow of cells into the buffer exchange device. At the entrance to the buffer exchange device, the flow bifurcates to form the outer streams of a sheath flow. A second pump 32 (e.g., a syringe pump) drives the flow of electroporation buffer containing cargo from the reservoir 22 to be delivered to the cells (mRNA, pDNA, RNP, etc.) into the center stream of the sheath flow in the buffer exchange device. An acoustic field driven by a piezoelectric actuator driven by the acoustic function generator 42 attached to the device drives cells from the outer streams into the center stream, into the cargo-containing, low-conductivity electroporation buffer. The entire sheath flow then passes into a flow electroporation module (which can be directly integrated into the buffer exchange device), where electrodes in contact with the outer streams are energized to expose the cells to electric fields. In other arrangements, it is just the center stream that passes into the electroporation device, with fresh high-conductivity buffer being introduced into the side streams. The outer streams then flow to waste, while the center stream is introduced into a second buffer exchange device. At the entrance to the second buffer exchange device, the flow coming from the electroporation module bifurcates to form the outer streams of a sheath flow. A pump 36 (e.g., a syringe pump) pumps cell culture or recovery buffer from the cell media reservoir 26 into the second rapid buffer exchange device to form the center of a sheath flow. An acoustic field driven by a piezoelectric actuator driven by the acoustic function generator 42 then drives the cells from the outer streams into the center stream, returning them to a culture buffer which can be the same or different from the initial buffer in the blood bag in the first incubator. The cells then flow into a collection receptacle in a second incubation chamber 20.

To facilitate or enhance the transfer of the payload into permeabilized cells, applying acoustic energy (using a sonicator, for example) can increase collisions between cells and the cargo material, thereby increasing the probability of bringing the cell and cargo material in close proximity and loading the cargo into the cells. An increase in the collision rate between cells and cargo also can be obtained using mechanical agitation or other suitable means. This happens naturally in the acoustic buffer exchange modules, but additional acoustic agitation can be added (e.g., using a piezoelectric transducer bonded to the outside of the device) to the flow electroporation device shown in FIG. 3.

Some embodiments provide for multiple buffer exchanges and/or multiple delivery events (multiple electroporation operations) to take place before cells are returned to the culture buffer in an incubator. This may require additional buffer exchange modules, flow electroporation modules, and pumps. At least some of the various transfers of cells into the electroporation buffer(s), electroporation, and transfer of cells out of electroporation buffer(s) back into a suitable cell culture buffer can be integrated into a single module.

In many embodiments, processes carried out in system 10 are conducted in continuous fashion. Since the system can be modular, it can be customized based on the application. For example, some processes may require only a single buffer exchange, while others may require several sequential buffer exchanges and several electroporation events for delivery of multiple payloads in sequence.

In yet other embodiments, the cells and/or reagents are recirculated for multiple passes.

Principles described herein also can be employed to remove some or all the contents held in cells or other membrane bound structures; that is, opening pores and allowing the internal contents to diffuse out either passively or via an active force.

As with conventional bulk electroporation techniques, the flow arrangement described herein remains compatible with the electroporation of cells in small batches. However, this is time and touch-labor intensive and will be intractable for large-scale processing.

Equipment and techniques described herein can increase throughput and/or improve the efficiency with which cargo is transferred to cells or other membrane bound structures. As described, various measures are taken to protect cells before, during and after the electroporation process, improving cell viability.

Thus, in some embodiments, cell electroporation can be conducted with a throughput of at least 4 million cells processed per minute, e.g., a throughput within the range of from about 4 million to about 50 million cells per minute. Transfection efficiencies for a genetic cargo such as mRNA to primary human T cells can be as high as 90% (with less than a 5% reduction in cell viability), within the range of from about 65% to about 90%, as indicated by expression of a fluorescent reporter protein measured by flow cytometry. In some cases, the efficiency of transferring cargo to cells can be increased by raising the cargo concentration, by promoting collisions between cells and cargo, increasing the electric field dosage (potentially at the cost of viability) and/or optimizing the electroporation buffer.

Cell viability, measured, for example, by flow cytometry, can be as high as 95% of the initial cell viability, within the range of from about 80% to about 95%, for instance.

Features described herein are consistent with scale up and commercial manufacturing goals and thus, embodiments described herein can find many applications. Examples include but are not limited to the production of Autologous or Allogeneic CAR-T, Allogeneic or Autologous TCR, TRnC cells, modified TILs, CAR-NKTs, CAR-NKs, CAR-Macs, CAR-CIK or modified gamma delta cells. The features described herein can also be used to engineer cargo-loaded exosomes, or produce gene modified stem or suspension cells to treat genetic diseases or disorders.

One illustrative application relates to cellular therapy manufacturing.

Recent developments in adoptive cell transfer based immunotherapies have increased the demand for improved cell bioprocessing and gene delivery technologies. For instance, the FDA has granted approval for the use of T cells modified to express chimeric antigen receptor (CAR) genes for treatment of certain hematological cancers. However, the manufacturing chain for CAR T cell based therapeutics currently involves lentiviral-based transduction for gene delivery. These vectors are complex and expensive to manufacture and have limited payload capacity. Since they integrate genetic information into the genome in an uncontrolled way this approach also presents safety concerns.

To address some of these problems, the non-limiting example below was conducted to investigate the feasibility of using embodiments described herein in the electrotransfection of primary human T cells for cellular therapy manufacturing.

EXAMPLE

Experiments were conducted using an assembly such as described above with reference to FIGS. 6-13.

In more detail, the assembly was constructed by laminating a stack of machined thin polymer layers together. Sheets of polyetherimide (PEI) were then machined either on a conventional CNC milling machine or an ultraviolet laser cutter. Each layer is backed with a layer of adhesive.

To demonstrate proof of concept, the arrangement used was simplified and did not include a buffer exchange function. Rather, a microfluidic hydrodynamic sheath flow configuration was established by directing a low-conductivity electroporation buffer containing primary human T cells and mCherry-encoding mRNA (CleanCap mCherry mRNA, Tri-Link Biotechnologies, San Diego, CA) through the central inlet (inlet 46c in FIG. 3). High-conductivity culture buffer was supplied through the two side inlets (46a, 46b in FIG. 3).

The cells and media entered and exited the microchannel through ports at the upstream and downstream ends, respectively. Stainless steel (SS) tubing was inserted and epoxied in place at the fluid inlets and outlets. Each inlet and outlet had a trifurcation design which allowed for the generation of a stable sheath flow configuration wherein cells entered the center inlet in low-conductivity media and high-conductivity buffer was run in both side inlets, surrounding the center flow. Metal electrodes that were sputter-deposited on the floor of the channel were connected to external control circuitry by soldered wire leads. The patterned electrodes were rectangular in geometry and were positioned to make contact only with the sheath fluid. The arrangement facilitated a concentration of the electric field across the width of the low-conductivity media (negligible voltage drop across the high-conductivity buffer) and prevented the cells from making physical contact with the electrodes and the sidewalls of the channel. This was believed to promote cell recovery and viability.

Experiments were conducted to investigate how electric field pulse magnitude, pulse duration, and the number of pulses applied affect transfection efficiency of mRNA into primary human T cells and the concomitant changes in cell viability and overall cell recovery. Higher electric field pulse magnitudes, and with longer exposure times, were found to increase transfection efficiency. According to one set of data, no transfection could be observed for field magnitudes of 67 kV/m and below. Transfection efficiency increased with increasing field magnitude in all cases starting at a magnitude of 102 kV/m. This suggested a critical electric field magnitude between 67 kV/m and 102 kV/m for transfection of mRNA into primary human T cells in this particular device.

Generally, the data showed that it was possible to electroporate the cells in a continuous flow arrangement. A throughput of up to $8 \times 10^6$ primary cells could be processed per minute, while achieving 72% electroporation efficiency as measured by the expression of a fluorescent reporter (mCherry) 24 hours after mRNA delivery. The cell viability was observed to be reduced by only 9% by the electroporation process and the total system recovery of cells was 61%.

Figure 14A:
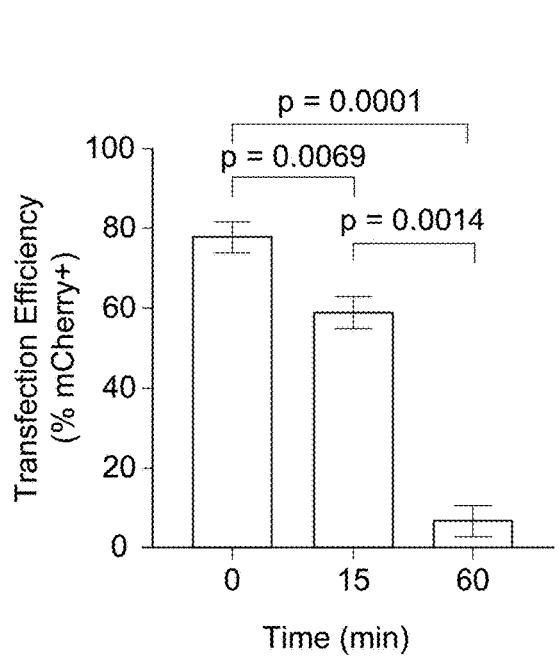
FIGS. 14A and 14B present, respectively, the transfection efficiency and viability data for T cells electroporated according to procedures described herein.
Figure 14B:
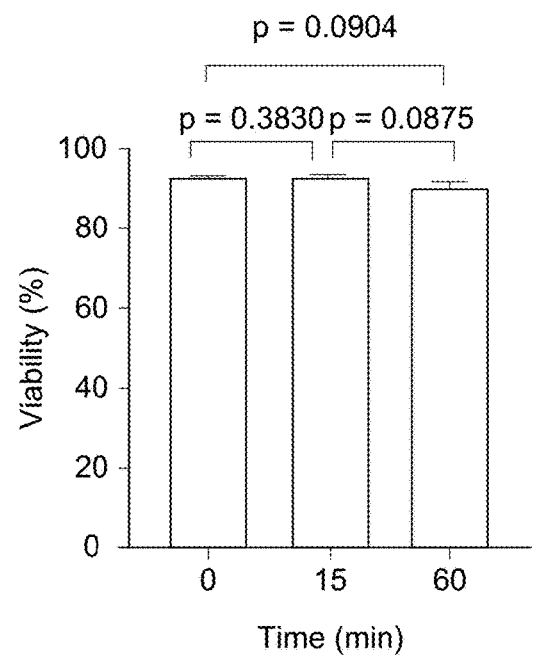

In specific examples, primary human T cells were electroporated using a commercial bulk electroporation system after being held in BTX electroporation media for 0, 15, or 60 minutes. Data is presented in FIGS. 14A and 14B, which shows average of replicates from 3 independent, healthy donors. Error bars represent the standard error of the mean. As seen in FIG. 14A, transfection efficiency, as measured by flow cytometry 24 hours after electroporation, is reduced when T cells are held in BTXpress media with mRNA for 15 min, and is reduced further if the hold time is increased to 60 min.

Post-transfection viability (FIG. 14B), as measured by flow cytometry 24 hours after electroporation, decreased with increasing hold time, but the decrease is not statistically significant.

Figure 15:
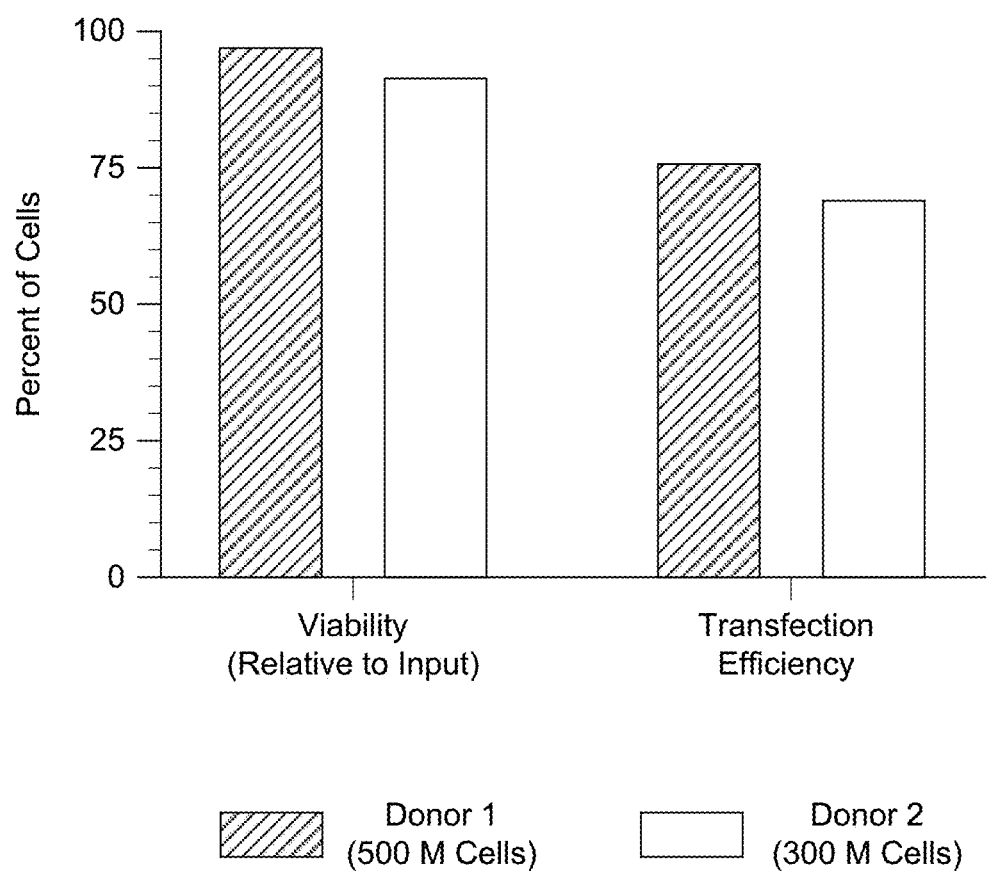
FIG. 15 shows viability and transfection efficiency of cells obtained from two donors and electroporated according to procedures described herein.

FIG. 15 shows the viability and transfection efficiency (as percent of cells) for cells obtained from two different donors similarly electroporated in continuous flow according to aspects of the invention.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for introducing a payload into cells, the method comprising:
   directing cells from a first incubator to an assembly that contains multiple microfluidic devices;
   acoustically driving cells from a cell culture medium flowing in a side stream of a sheath flow configuration, to an electroporation medium flowing through a central stream of the sheath flow configuration;
   applying an electric field to cells in the electroporation medium; and
   transferring or allowing the transfer of the payload into the cells.

2. The method of claim 1, further comprising driving cells containing the payload from the electroporation fluid into a cell culture fluid.

3. The method of claim 2, further comprising storing cells containing the payload in a second incubator.

4. The method of claim 1, further comprising administering cells containing the payload to a subject in need of diagnosis, prophylaxis or treatment.

5. The method of claim 1, wherein the payload is supplied in the electroporation medium.

6. The method of claim 1, further comprising driving cells containing the payload from the electroporation medium to a third medium.

7. The method of claim 1, wherein the electric field is applied by a pair of electrodes provided for each microfluidic device in the assembly.

8. A method for manufacturing cells for immunotherapy, the method comprising:
   acoustically transferring cells from a first buffer, wherein the first buffer is a cell culture medium, into an electroporation buffer;
   permeabilizing the cells by electroporation;
   allowing a payload to transfer into the permeabilized cells; and
   transferring the cells containing the payload into a second buffer, wherein, the method is conducted in an automated and continuous flow mode, wherein the electroporation buffer forms a central stream and the first buffer forms a side stream of a sheath flow configuration, and wherein, the throughput is at least 4 million cells per minute.

9. The method of claim 8, wherein the method is conducted in an assembly comprising multiple microfluidic devices.

10. A method for introducing a payload into cells, the method comprising:
    flowing an electroporation medium as a central stream of a sheath flow configuration;
    flowing a first medium containing cells as a side stream in the sheath flow configuration;
    applying acoustic energy to drive cells from the first medium to the electroporation medium;
    applying an electric field to permeabilize the cells in the electroporation medium; and allowing the payload to transfer into the permeabilized cells.

11. The method of claim 10, further comprising driving the cells containing the payload from the electroporation medium to the first medium.

12. The method of claim 10, further comprising driving the cells containing the payload from the electroporation medium to a second medium, wherein the second medium is a central stream in a sheath flow configuration.

13. The method of claim 10, further comprising applying a second acoustic energy to drive cells containing the payload from the electroporation medium to a second medium flowing as a center stream in a sheath flow configuration.

14. The method of claim 10, wherein the method is conducted in a microfluidic device or in an assembly comprising multiple microfluidic devices.

15. The method of claim 10, wherein the first medium containing cells is supplied from an incubator.

16. The method of claim 10, wherein the payload is provided in the electroporation medium.

17. The method of claim 10, wherein the method is conducted in an automated continuous flow mode.

18. The method of claim 10, further comprising administering the cells containing the payload to a patient in need of diagnosis, prophylaxis or treatment.

\* \* \* \* \*